(12) United States Patent
Johnson et al.

(10) Patent No.: US 7,534,806 B2
(45) Date of Patent: May 19, 2009

(54) METHOD FOR TREATING NEUROPATHIC PAIN AND ASSOCIATED SYNDROMES

(75) Inventors: Kirk W. Johnson, Moraga, CA (US); Lance Sultzbaugh, San Francisco, CA (US); Jennifer Shumilla, San Mateo, CA (US)

(73) Assignee: Avigen, Inc., Alameda, CA (US)

( * ) Notice: Subject to any disclaimer, the term of this patent is extended or adjusted under 35 U.S.C. 154(b) by 0 days.

(21) Appl. No.: 11/295,730

(22) Filed: Dec. 6, 2005

(65) Prior Publication Data

US 2006/0160843 A1 Jul. 20, 2006

Related U.S. Application Data

(60) Provisional application No. 60/634,248, filed on Dec. 6, 2004, provisional application No. 60/665,276, filed on Mar. 25, 2005, provisional application No. 60/716,333, filed on Sep. 12, 2005.

(51) Int. Cl.
*A01N 43/56* (2006.01)
(52) U.S. Cl. .................................................. 514/406
(58) Field of Classification Search ................. 514/406, 514/816–819, 903
See application file for complete search history.

(56) References Cited

U.S. PATENT DOCUMENTS

| | | | |
|---|---|---|---|
| 4,735,954 A | 4/1988 | Irikura et al. | |
| 6,136,839 A | 10/2000 | Isakson et al. | |
| 6,395,747 B1 * | 5/2002 | Sakoda | 514/300 |
| 2002/0068740 A1 | 6/2002 | Mylari et al. | |
| 2002/0137755 A1 | 9/2002 | Bilodeau et al. | |
| 2003/0050301 A1 | 3/2003 | Mylari | |
| 2003/0087938 A1 * | 5/2003 | Robertson | 514/357 |
| 2003/0144298 A1 | 7/2003 | Curwen et al. | |
| 2004/0014761 A1 | 1/2004 | Place et al. | |
| 2004/0023290 A1 | 2/2004 | Griffon et al. | |
| 2004/0053842 A1 | 3/2004 | Nguyen et al. | |
| 2004/0063685 A1 | 4/2004 | Ilzawa et al. | |
| 2004/0063720 A1 | 4/2004 | Bilodeau et al. | |
| 2004/0063946 A1 | 4/2004 | Ohkawa et al. | |
| 2004/0097555 A1 | 5/2004 | Ohkawa et al. | |
| 2004/0138223 A1 | 7/2004 | Nakamura et al. | |
| 2004/0186083 A1 | 9/2004 | McMahon et al. | |
| 2004/0192584 A1 | 9/2004 | McMahon et al. | |
| 2004/0235822 A1 | 11/2004 | Shiraishi et al. | |
| 2004/0242455 A1 | 12/2004 | Okazaki et al. | |
| 2004/0253276 A1 | 12/2004 | Sato et al. | |
| 2004/0266743 A1 | 12/2004 | McMahon et al. | |
| 2005/0004096 A1 | 1/2005 | Torisu et al. | |
| 2005/0004097 A1 | 1/2005 | Torisu et al. | |
| 2005/0014787 A1 | 1/2005 | Uchida et al. | |
| 2005/0080113 A1 | 4/2005 | Ohkawa et al. | |
| 2005/0119160 A1 | 6/2005 | Keith et al. | |
| 2005/0124577 A1 | 6/2005 | Tani et al. | |

FOREIGN PATENT DOCUMENTS

| | | |
|---|---|---|
| EP | 215438 B1 | 3/1987 |
| EP | 1106210 A2 | 6/2001 |
| EP | 1318140 A1 | 3/2002 |
| EP | 1336602 A1 | 3/2003 |
| EP | 1348443 A1 | 10/2003 |
| EP | 1354603 A1 | 10/2003 |
| EP | 1402900 A1 | 3/2004 |
| EP | 1415983 A1 | 5/2004 |
| EP | 1424325 A1 | 6/2004 |
| EP | 1424335 A1 | 6/2004 |
| EP | 1443041 A1 | 8/2004 |
| EP | 1481976 A1 | 12/2004 |
| EP | 1498125 A1 | 1/2005 |
| WO | WO 96/41626 A1 | 12/1996 |
| WO | WO 99/64037 A1 | 12/1999 |
| WO | WO 01/74360 A1 | 10/2001 |
| WO | WO 01/74811 A1 | 10/2001 |
| WO | WO 02/45652 A1 | 6/2002 |
| WO | WO 02/098429 A1 | 12/2002 |
| WO | WO 03/092595 A2 | 11/2003 |
| WO | WO 2004/004778 A1 | 1/2004 |
| WO | WO 2004/041164 A2 | 5/2004 |
| WO | WO 2004/060283 A2 | 7/2004 |
| WO | WO 2004/067006 A1 | 8/2004 |
| WO | WO 2004/082636 A2 | 9/2004 |
| WO | WO 2004/082637 A2 | 9/2004 |
| WO | WO 2004/098538 A2 | 11/2004 |
| WO | WO 2004/100871 A2 | 11/2004 |
| WO | WO 2005/027839 A2 | 3/2005 |
| WO | WO 2005/037203 A2 | 4/2005 |
| WO | WO 2005/051293 A2 | 6/2005 |

OTHER PUBLICATIONS

Andersen et al. "Incidence of central post-stroke pain"; 1995, Pain, vol. 61, pp. 187-193.*
Backonja, Misha-Miroslav "Use of anticonvulsants for treatment of neuropathic pain"; 2002, Neurology, vol. 59, pp. S14-S17.*
Burnouf, et al., "Recent Advances in PDE4 Inhibitors as Immunoregulators and Anti-Infammatory Drugs," *Curr Pharma Design* 8:1255-1296 (2002).
Castro, et al., "Cyclic Nucleotide Phosphodiesterases and Their Role in Immunomodulatory Responses: Advances in the Development of Specific Phosphodiesterase Inhibitors," *Medicinal Res Rev* 25 (2):229-244 (2005).
Fukuyama, et al., "Pharmacological Effects of Ibudilast on Cerebral Circulation: a PET Study," *Neurol Res* 15(3):169-173 (1993).
Fujimoto, et al., "Ibudilast, A Phosphodiesterase Inhibitor, Ameliorates Experimental Autoimmune Encephalomyelitis in Dark August Rats," *J Neuroimmunology* 95:35-42 (1999).

(Continued)

*Primary Examiner*—Sreeni Padmanabhan
*Assistant Examiner*—Kendra D Carter
(74) *Attorney, Agent, or Firm*—Robins & Pasternak LLP

(57) ABSTRACT

The present invention is directed to the use of ibudilast for treating neuropathic pain.

15 Claims, 8 Drawing Sheets

OTHER PUBLICATIONS

Ganbo, et al., "Effect of Ibudilast on Ciliary Activity of Human Paranasal Sinus Mucosa In Vitro," *Arzneimillel-Forschung* 45(8):883-886) (1995).

Gauthier, et al., "The Differential Effects of Biofeedback in the Treatment of Menstrual and Nonmenstrual Migraine," *Headache* 3182-90 (1991).

Graul, et al., "Montelukast Sodium. Antiallergic/Antiasthmatic Leukotrine CysLT1 Antagonist," *Drugs of the Future* 22(10):1103-1111 (1997).

He, et al., "Novel Cyclic Compounds as Potent Phosphodiesterase 4 Inhibitors," *J Med Chem* 41:4216-4223 (1998).

Hoshino, et al., "Inhibitory Effect of Ibudilast on Urinary Albumin Excretion in Type 2 Diabetes Mellitus with Microalbuminuria," *Nephron* 90:154-157 (2002).

Ichinose, et al., "Antiasthma Drug, Ibudilast, Inhibits Neurogenic Plasma Extravasation in Guinae-Pig Airways," *American Review of Respitory Disease* 148(2):431-434 (1993).

Ikeda, et al., "Daily Cost of Ophthalmic Solutions Used to Treat Allergic Conjunctivitis in Japan," *Ophthalmic Epidemiology* 11(1):35-42 (2004).

Kagitani-Shimono, et al., "Anti-Inflammatory Therapy by Ibudilast, a Phosphodiesterase Inhibitor, in Demyelination of Twitcher, a Genetic Demyelination Model," *BioMed Central* 1-12 (2005).

Kishi, et al., "Ibudilast: A Non-Selective PDE Inhibitor with Multiple Actions on Blood Cells and the Vascular Wall," *Cardiovasc Drug Rev* 19(3):215-225 (2001).

Kunika, "Studies on Sensory Nerve Conduction Velocity, Blood Flow, and Fiber Degeneration of the Sciatic Nerve in Streptozotocin-Induced Diabetic Rat," *St Mariann Med J* 23:582-592 (1995)*English translation and original Japanese article.*

Mizuno, et al., "Neuroprotective Role of Phosphodiesterase Inhibitor Ibudilast on Neuronal Cell Death Induced by Activated Microglia," *Neuropharma* 46:404-411 (2004).

Nishino, et al., "KC-404: a Potent Anti-Allergic Agent with Antagonistic Action Against Slow Reacting Substance of Anaphylaxis," *Japanese Journal of Pharmacology* 33(2):267-278 (1983).

Niwa, et al., "Ibudilast, an Anti-Allergic and Cerebral Vasodilator, Modulates Superoxide Production in Human Neutrohils," *Life Sciences* 56(2):107-115 (1995).

Obernolte, et al. "The cDNA of a Human Lymphocyte Cyclic-AMP Phosphodiesterase (PDA IV) Reveals a Multigene Family," *Gene* 129:239-247 (1993.

Ochai, et al., "Discovery of New Orally Active Phosphodiesterase (PDE4) Inhibitors," *Chem Pharm Bull* 52(9):1098-1104 (2004).

Ohashi, et al., "Antagonistic Effect of KC-404, a New Anti-Asthmatic Agent, On Leukotrine D-4 Induced Contractile Responses in Isolated Guinea Pig Smooth Muscle," *Prostaglandins* 32(6):875-888 (1986).

Ohashi, et al., "Effect of Ibudilast, A Novel Antiasthmatic Agent, On Anaphylactic Bronchoconstriction: Predominant Involvement of Endogenous Slow Reacting Substance of Anaphylaxis," *Internat Arch Aller Immunol* 101(3):288-296 (1993).

Ohshima, "Therapeutic Effect of Amelioration of Peripheral Blood Flow on Motor Nerve Conduction Velocity in Experimental Diabetic Rats," *St Marianna Med J* 22:274-282 (1994) *English translation, original Japanese article and English abstract.*

Park, et al., "The Effects of Ibudilast on Diabetic Peripheral Neuropathy," *Jpn Pharmacol Ther* 19(5):2033-2037 (1991) *English translation, original Japanese article and English abstract.*

Park, "The Effects of Ibudilast on Diabetic Peripheral Neuropathy, Part 2" *Jpn Pharmacol Ther* 23(6):133-139 (1995) *English translation, original Japanese article and English abstract.*

Rile, et al., "Potentiation of Ibudilast Inhibition of Platelet Aggregation in the Presence of Endothelial Cells," *Thromb Res* 102:239-246 (2001).

Shimomura, et al., "Anelgesic Induced Headaches: Successful Treatment with Ibudilast," *Geriatr Med* 29(2):315-323 (1991) *Original Japanese Only.*

Shimomura, et al., "Anelgesic-Induced Headaches: Successful Treatment with Ibudilast," *Headache* 31:483 (1991).

Sone, et al., "Efficacy of Ibudilast on Lower Limb Circulation of Diabetic Patients with Minimally Impaired Baseline Flow: A Study Using Color Doppler Ultrasonography and Laser Doppler FLowmetry," *Angiology* 46(8):699-703 (1995).

Souness, et al., "Potential of Phosphodiesterase Type 4 Inhibitors in the Treatment of Rheumatoid Arthritis," *Curr Res Rhuem Arthritis* 2(6):255-268 (1998).

Souness, et al., "Possible Role of Cyclic AMP Phosphodiesterases in the Actions of Ibudilast on Eosinophil Thromboxane Generation and Airways Smooth Muscle Tone," *Br. J Pharmacol* 111:1081-1088 (1994).

Sugiyama, et al., "SPECT Evaluation Of Effect Of Cerebral Vasodilator By The Subtraction Method Using Tc-99m HMPAO," *No To Shinkei* 45(2):139-142 (1993) *Original Japanese article and English abstract.*

Sunada, et al., "The Role of Leukotrienes in Ocular Inflammation Report 2. The Effect of Anti-SRS-A Substance (KC-404) on Experimental Uveitis in Guinea Pigs," *Nippon Ganka Gakkai Zasshi Acta Societatis Opthamologicae Japonicae* 88(11):1341-1349 (1984) *Original Japanese article and English abstract.*

Suzumura, et al., "Ibudilast Suppresses TNF α Production by Glial Cells Functioning Mainly as Type III Phosphodiesterase Inhibitor in CNS," *Brain Res* 837:203-212 (1999).

Szekely, "More on Perimenstrual Migraine," *Headache* 31:484-485 (1991).

Takuma, "Delayed Apoptosis and Its Regulation in Astrocytes," *Yakugaku Zasshi* 121(9):663-669 (2001) *English translation, Original Japanese article and English abstract.*

Takuma, et al., "Ibudilast Attenuates Astrocyte Apoptosis Via Cyclic GMP Signalling Pathway in an In Vitro Reperfusion Model," *Br J Pharmacol* 133:841-848 (2001).

Tominaga, et al., "Ibudilast Protects Against Neuronal Damage Induced by Glutimate in Cultured Hippocampal Neurons," *Clin Exper Pharmacol Physiol* 23(6-7):519-523 (1996).

Tsuneichi, et al., "Effect of Continuos Oral Administration of KC-764 on Monoamines, Acetylcholine and Neuroactive Amino Acids Contents in Rat Brain," *Clinical Report* 28(8):113-119 (1994) *Original Japanese article and English abstract.*

Watkins, et al., "Targeting Glia to Control Clinical Pain: An Idea Whose Time has Come,"*Drug Disc Today* 1(1):83-88 (2004).

Watkins, et al., "A Novel Drug Discovery Target for Clinical Pain," *Nature Reviews Drug Discov* 2:973-985 (2003).

Watkins, et al., "Beyond Neurons: Evidence That Immune and Glial Cells Contribute to Pathological Pain States," *Physiol Rev* 82:981-1011 (2002).

Wieseler-Frank, et al., "Glial Activation And Pathological Pain," *Neurochem Int* 45:389-395 (2004).

Yamauchi, "Effects of Ibudilast on Diabetic Neuropathy. Subjective and Objective Improvement by Ibudilast," *Clin Res* 71(9):2492-2502 (1994) *English translation and original Japanese article.*

Yanase, et al., "Ibudilast Reduces Intracellular Calcium Elevation Induced by In Vitro Ischeamia in Gerbil Hippocampal Slices," *Clin Exper Pharmacol Physiol* 23(4):317-324 (1996).

Yasaki, et al., "Effect of Ibudilast on Experimental Diabetic Neuropathy," *J Japan Diab Soc* 37(3):215-222 (1994) *English Translation, original Japanese article and English anstract.*

Yoshioka, et al., "Ibudilast Prevents Oligodendroglial Excitotoxicity," *Brain Nerve* 49(11):1015-1020 (1997) *Original Japanese article and English abstract.*

Yoshioka, et al., "Cyclic AMP-Elevating Agents Prevent Oligodendroglial Excitotoxicity," *J Neurchem* 70:2416-2423 (1998).

Yoshioka, et al., "Effects of Ibudilast on Hippocampal Long-Term Potentiation and Passive Avoidance Responses in Rats with Transient Cerebral Ischemia," *Pharmacol Res* 45(4):305-311 (2002).

Feng, et al., "Ibudilast, A Nonselective Phosphodiesterase Inhibitor, Regulates TH1/TH2 Balance and NKT Cell Subset in Multiple Sclerosis," Multiple Scierosis, 10:494-498 (2004).

Medicinova Announces Positive Clinical Results From MN-166 Phase II Multiple Sclerosis Trial, MediciNova Press Release, 2 pages, Mar. 27, 2007.

\* cited by examiner

GFAP Staining; Rat Lumbar Spinal Cord Tissue

CCI vehicle            CCI ibudilast (7.5 mg/kg)

METHOD FOR TREATING NEUROPATHIC PAIN AND ASSOCIATED SYNDROMES

CROSS REFERENCE TO RELATED APPLICATIONS

This application claims the benefit of priority to each of the following provisional applications: Provisional Application No. 60/634,248, filed Dec. 6, 2004; Provisional Application No. 60/665,276, filed Mar. 25, 2005, and Provisional Application No. 60/716,333, filed Sep. 12, 2005, the contents of which are expressly incorporated herein by reference in their entireties.

FIELD OF THE INVENTION

The present invention relates generally to methods for treating neuropathic pain. In particular, the present invention pertains to methods of treating or preventing neuropathic pain and its associated symptoms by administration of ibudilast (3-isobutyryl-2-isopropylpyrazolo[1,5-a]pyridine).

BACKGROUND OF THE INVENTION

In recent years, pain management has become an area of increasing focus in the medical profession, partly due to the growing population of elderly, issues surrounding quality of life, and the growing numbers of patients reportedly suffering from pain. Pain is both a sensory and emotional experience, and is generally associated with tissue damage or inflammation. Typically, pain is divided into two general categories—acute pain and chronic pain. Both differ in their etiology, pathophysiology, diagnosis, and most importantly, treatment.

Acute pain is short term, and is typically of a readily identifiable cause. Patients suffering from acute pain typically respond well to medications. In contrast, chronic pain, medically-defined as pain that lasts for 3-6 months or longer, is often not associated with an obvious injury; indeed, patients can suffer from protracted pain that persists for months or years after the initial insult. While acute pain is generally favorably treated with medications, chronic pain is often much more difficult to treat, generally requiring expert care. Reportedly, according to the American Chronic Pain Association, over 86 million Americans suffer from chronic pain, and the management of chronic pain has long been recognized as an unmet clinical need. Most chronic pain is neuropathic in nature (also referred to as neuralgia). Neuropathic pain can, for instance, manifest itself as burning, stabbing, and shock-like sensations.

Unfortunately, neuropathic pain management is at best inconsistent, and often times ineffective. This is in part due to the subjective nature of pain, but also due to poor diagnosis, especially when the chronic pain is not clearly associated with a nerve injury or other insult. Moreover, few, if any, ethical drugs have been prospectively developed for the treatment of chronic pain. Instead, the current medications used to treat chronic pain are "borrowed" from other diseases, most commonly antiepileptic drugs and antidepressants.

Current first-line treatments for chronic pain include opioids, analgesics such as gabapentin, and tricyclic antidepressants. In the instance of opioids, when administered over prolonged periods, undesirable side effects such as drug tolerance, chemical dependency and even physiological addiction can occur. Of treatment regimes currently available for chronic pain, at best, approximately 30% are effective in significantly diminishing the pain, and may lose their efficacy over time. Although numerous pharmacological agents are available for the treatment of neuropathic pain, a definitive therapy has remained elusive.

In instances in which treatment with a single agent proves to be unsuccessful, combination therapy is often then explored as a second line treatment. For example, such combination therapy may employ administration of an opioid agent with an adjuvant analgesic, although the relative doses of each are often subject to prolonged trial and error periods. Oftentimes, triple drug therapy is necessary. Such therapy generally involves a combination of tricyclic antidepressants, anti-convulsants, and a systemic local anesthetic. Patient compliance drops significantly, however, when treatment requires the administration of multiple pharmacologic agents. Recently, researchers reported the use of a combination of morphine and gabapentin in a randomized study for controlling nerve pain (Gilron, I., et al., *New Eng. J of Medicine*, Vol 352:1281-82, No. 13, Mar. 31, 2005).

Moreover, it is not only important to consider overall pain relief, but also the type of pain relief. For example, chronic pain is typically viewed as allodynia or hyperalgesia. Allodynia is pain sensation from a stimulus that is not normally painful. The allodynia is typically caused by a physical stimulus and thus referred to as tactile or mechanical allodynia. Hyperalgesia is an exaggerated sensation from a stimulus that is normally painful. The hyperalgesia can occur from a variety of stimuli, but commonly, a patient's reaction to hot and cold stimuli is reported. Importantly, physicians often report that the current drugs are most effective at relieving hyperalgesia although most patients complain from allodynia, particularly mechanical allodynia.

In addition to poor and/or inconsistent efficacy, these medications have several other undesirable properties, such as adverse events, duration of action, and complicated dosing and titration regiments.

The most common side-effect of the non-opiate drugs is sedation or somnolence. Based on data from the package inserts for these drugs, as many as 20-30% of patients experience sedation. As mentioned above, the population greatest at risk for chronic pain are elderly. For the elderly, experiencing significant and persistent sedation poses other risks, mainly locomotors function impairment. Such locomotors function impairment can lead to falling and the inability to perform many daily functions such as driving.

The duration of action is also a limitation for most of the leading therapies. This is particularly important as pain, and especially nighttime pain, can lead to depression, insomnia and other factors that impact the patient's overall quality of life. A recent study suggests that patients with chronic pain and concurrent major depression and insomnia report the highest levels of pain-related impairment. This study also found that insomnia in the absence of major depression is also associated with increased pain and distress. (Wilson et al., *Clin J Pain* 2002 March.-April.; 18(2):77-83.). Therefore, achieving pain relief with a sufficient duration to achieve relief through the night is an important factor for neuropathic pain drugs. Pain-relief drugs such as gabapentin are taken once or more during the night to achieve pain relief—thus disturbing sleep and exacerbating the patient's overall quality of life.

Finally, the dosing or titration of the leading drugs, such as gabapentin, can be complicated. For example, the recommended starting dose for gabapentin in adults with postherpetic neuralgia is a single 300-mg dose on Day 1, 600 mg/day on Day 2 (divided BID), and 900 mg/day on Day 3 (divided TID). If no relief is obtained at these doses, the dose can subsequently be titrated up as needed for pain relief to a daily dose of 1800 mg (divided TID). In clinical studies, efficacy was demonstrated over a range of doses from 1800 mg/day to 3600 mg/day with comparable effects across the dose range." (Neurontin® Full U.S. Prescribing Information). Other anti-epileptic drugs and antidepressants have similar dosing schedules which are similarly complicated, discourage compliance, and increase the chances of incorrect dosing and even overdosing. Further, discontinuing such drugs can also be challenging. For instance, as stated on the Full U.S. Prescribing Information for Neurontin® " . . . [A]s dose is reduced, discontinued or substituted with an alternative medication, this should be done gradually over a minimum of 1 week."

Neuropathic pain (NP) is generally thought of as a maladaptive chronic condition in which pain originates from damaged nerves, often yielding pain that is out-of-proportion to the extent of injury. The damage can occur from a physical injury such as trauma or from chemical injury such as chemotherapeutics (e.g., paclitaxol). Neuropathic pain of this type is an important component of a number of syndromes of varying etiologies whose common characteristic is the development of a prolonged and profound pain state. Among these conditions are spinal cord injury, post-herpetic neuralgia, diabetic neuropathy, phantom limb pain, stump/neuroma pain, post-ischemic pain (stroke), fibromyalgia, reflex sympathetic dystrophy (RSD), complex regional pain syndrome (CRPS), cancer-chemotherapeutic induced neuropathic pain, vertebral disk rupture, trigeminal neuralgia, and others.

Recently, however, it has been recognized that neuropathic pain can manifest itself in the absence of an identifiable nerve injury. These indications include AIDS and mirror image pain. The lack of any nerve injury but unmistakable chronic pain has led to increased interest in the role of glial cells in the maintenance of the neuropathic pain state. (Watkins and Maier (2004) *Drug Disc. Today: Ther. Strategies* 1(1): 83-88). More specifically, recent research has demonstrated that glial enhance the release of neurotransmitters that relay pain information to the spinal cord, and, even more striking, release substances that increase the excitability of pain-responsive neurons in the spinal cord. These substances, called pro-inflammatory cytokines, create and maintain exaggerated or pathological pain responses. Blocking the activation of glia reduces pro-inflammatory cytokines and reverses pathological pain. To date, no therapeutics have been approved that have a putative glial-attenuation mechanism for the treatment of neuropathic pain. Molecules which are glial-attenuators may play an important role in treating neuropathic pain.

The small molecule, ibudilast, (3-isobutyryl-2-isopropylpyrazolo[1,5-a]pyridine), is a non-selective inhibitor of cyclic nucleotide phosphodiesterase (PDE) (Fujimoto, T., et al., *J. of Neuroimmunology*, 95 (1999) 35-92). Ibudilast also acts as an LTD4 antagonist, an anti-inflammatory, a PAF antagonist, and a vasodilatatory agent (Thompson Current Drug Reports). Ibudilast is thought to exert a neuroprotective role in the central nervous system of mammals, presumably via suppression of the activation of glial cells (Mizuno et al. (2004) *Neuropharmacology* 46: 404-411). Ibudilast has been widely used in Japan for relieving symptoms associated with ischemic stroke or bronchial asthma. Marketed indications for ibudilast in Japan include its use as a vasodilator, for treating allergy, eye tissue regeneration, ocular disease, and treatment of allergic ophthalmic disease (Thompson Current Drug Reports). In recent clinical trials, its use in the treatment of multiple sclerosis, an inflammatory disease of the central nervous system, has been explored (News.Medical.Net; Pharmaceutical News, 2 Aug. 2005). While the use of ibudilast for a number of varying indications has been reported to date, to the best of the applicants' knowledge, its use in treating neuropathic pain and conditions associated therewith, including allodynia, has heretofore remained largely unexplored.

In light of the above shortcomings in current approaches for treating chronic pain, there exists a need for improved compositions and methods for treating pain, particularly neuropathic pain and its associated symptoms, and more specifically, neuropathic pain associated with certain conditions such as fibromyalgia, among others. Such approaches should ideally overcome one or more of the problems associated with existing methods for treating chronic pain. The present invention meets these needs.

SUMMARY OF THE INVENTION

The present invention relates to a novel approach to treating neuropathic pain, and is based upon the surprising discovery that neuropathic pain can be successfully treated or prevented by administration of ibudilast. Using standard neuropathic pain models, the inventors have discovered that the systemic administration of ibudilast is effective in preventing and attenuating, if not eliminating, chronic neuropathic pain, such as that associated with various syndromes. In some instances, administration of ibudilast can provide an effective treatment for neuropathic pain-related conditions that are non-responsive to existing therapies. Further, ibudilast has been found to be effective in significantly attenuating mechanical allodynia for a duration lasting overnight—thus offering a significant advantage over existing chronic pain drugs such as gabapentin. Such durable efficacy is uncommon for most neuropathic pain drugs.

Accordingly, in one aspect, the invention provides a method of treating a mammalian subject suffering from neuropathic pain by administering to the subject a therapeutically effective amount of ibudilast.

In one embodiment, the method includes the step of selecting a mammalian subject experiencing neuropathic pain, followed by administering to the subject an initial therapeutic dosage of ibudilast effective to achieve a maximal plasma concentration of at least about 100 to 125 ng/ml ibudilast or higher, whereby as a result of such administering, the subject experiences relief (i.e., attenuation or reduction, elimination, or reversal) of the neuropathic pain.

Mammalian subjects suitable to be selected for treatment include those suffering from postherpatic neuralgia, trigeminal neuralgia, and neuropathic pain associated with a condition selected from the group consisting of herpes, HIV, traumatic nerve injury, stroke, post-ischemia, fibromyalgia, reflex sympathetic dystrophy, complex regional pain syndrome, and cancer-chemotherapeutic-induced neuropathic pain.

In one or more alternative embodiments, an initial therapeutic dosage of ibudilast is one effective to achieve a maximal plasma concentration of at least about 100, 125, 150, 175, 200, 225, 250, 275 or 300 ng/ml ibudilast.

In yet another embodiment of the method, ibudilast is administered at a daily dosage amount ranging from about 30 mg to 200 mg daily, or from about 30 mg to 100 mg daily.

The therapeutic dosage amount may be achieved by administration once daily (i.e., in a single dose), twice daily (i.e., in two separate doses), three times daily, or may be administered as multiple doses over a timecourse of several days, weeks, or even months. Such administering is typically over a duration of time effective to result in a diminution, and ideally elimination or even reversal, of neuropathic pain. Exemplary durations of treatment include at least about one week, from 1 week to 1 month, from two weeks to 2 months, up to about 6 months, up to about 12 months or even longer. In one particular embodiment, treatment lasts from about 1 week to about 50 weeks.

In a preferred embodiment of the treatment method, the administering is over a duration of time effective to result in elimination of the neuropathic pain.

Administration of ibudilast is effective, in yet another embodiment, to decrease an amount of neuropathic pain experienced by the subject for up to at least 16 hours post administration.

In yet another embodiment of the method, administration of ibudilast is not accompanied by administration of an antiemetic agent.

In a further embodiment of the method, ibudilast is administered in combination with at least one other agent effective for treating pain. Such agents agents include gabapentin, memantine, pregabalin, morphine and related opiates, cannabinoids, tramadol, lamotrigine, carbamazepine, duloxetine, milnacipran, and tricyclic antidepressants, among others. In a preferred embodiment, the secondary agent for treating neuropathic pain is one having a mechanism of action different from that of ibudilast.

In yet another embodiment, ibudilast, when administered either singly or as part of a combination therapy, is administered either systemically or centrally (e.g., by intrathecal administration, i.e., into the cerebrospinal fluid surrounding the spinal cord). Such administration of ibudilast provides a novel mechanism to attenuate pathologically painful conditions, potentially via suppression of glial activation.

According to yet a further embodiment, ibudilast is administered systemically, e.g. via intravenous, subcutaneous, oral, intranasal, sublingual or other systemic routes, to a mammalian, e.g., human, subject for the treatment of neuropathic pain, e.g., a neuropathic pain syndrome.

In another aspect, the invention provides a composition or combination effective for treating neuropathic pain. The composition comprises a combination of: (i) ibudilast, and (ii) at least one additional agent effective for treating neuropathic pain, where each of the components is either contained in a single composition or dosage form (such as in an admixture), or is present as a discrete or separate entity (e.g., in a kit).

A composition of the invention may optionally include one or more pharmaceutically acceptable excipients.

In yet another aspect, the invention encompasses a kit comprising a combination of medicaments for the treatment of neuropathic pain or a related syndrome, comprising, (i) ibudilast, and (ii) at least one additional agent effective for treating neuropathic pain, for simultaneous, sequential or separate use.

Each of the herein-described features of the invention is meant to apply equally to each and every embodiment as described herein, unless otherwise indicated.

Additional objects, advantages and novel features of the invention will be set forth in the description that follows, and in part, will become apparent to those skilled in the art upon reading the following, or may be learned by practice of the invention.

BRIEF DESCRIPTION OF THE FIGURES

FIG. 4A depicts the attenuation of allodynia after taxol-induced neuropathy is fully established. Data is the average of allodynia measurements in both hind paws. Data points represent the mean+/−standard error: taxol+35% PEG/saline (-■-); taxol+7.5 mg/kg ibudilast (filled circle). n≧5/group for allodynic animals and ≧2 for non-taxol normal controls. Mean value data points for ibudilast group at days 22, 24 and 25 are statistically significantly different from vehicle control by Students t test. FIG. 4B is a separate study and depicts the prevention of the development of allodynia when ibudilast administration (as per FIG. 4A) is initiated when the cancer chemotherapy-induced neuropathy is just beginning to develop ($12^{th}$ day after initiating taxol treatment). Data points represent the mean+/−standard error of allodynia measurements in hind limb. Non-taxol-treated, but taxol vehicle-treated, controls then treated with PEG/saline vehicle (triangle) or ibudilast (diamond) vs taxol-treated rats then administered PEG/vehicle (black square) or ibudilast 7.5 mg/kg i.p. BID (circle).

DETAILED DESCRIPTION OF THE INVENTION

Figure 1:
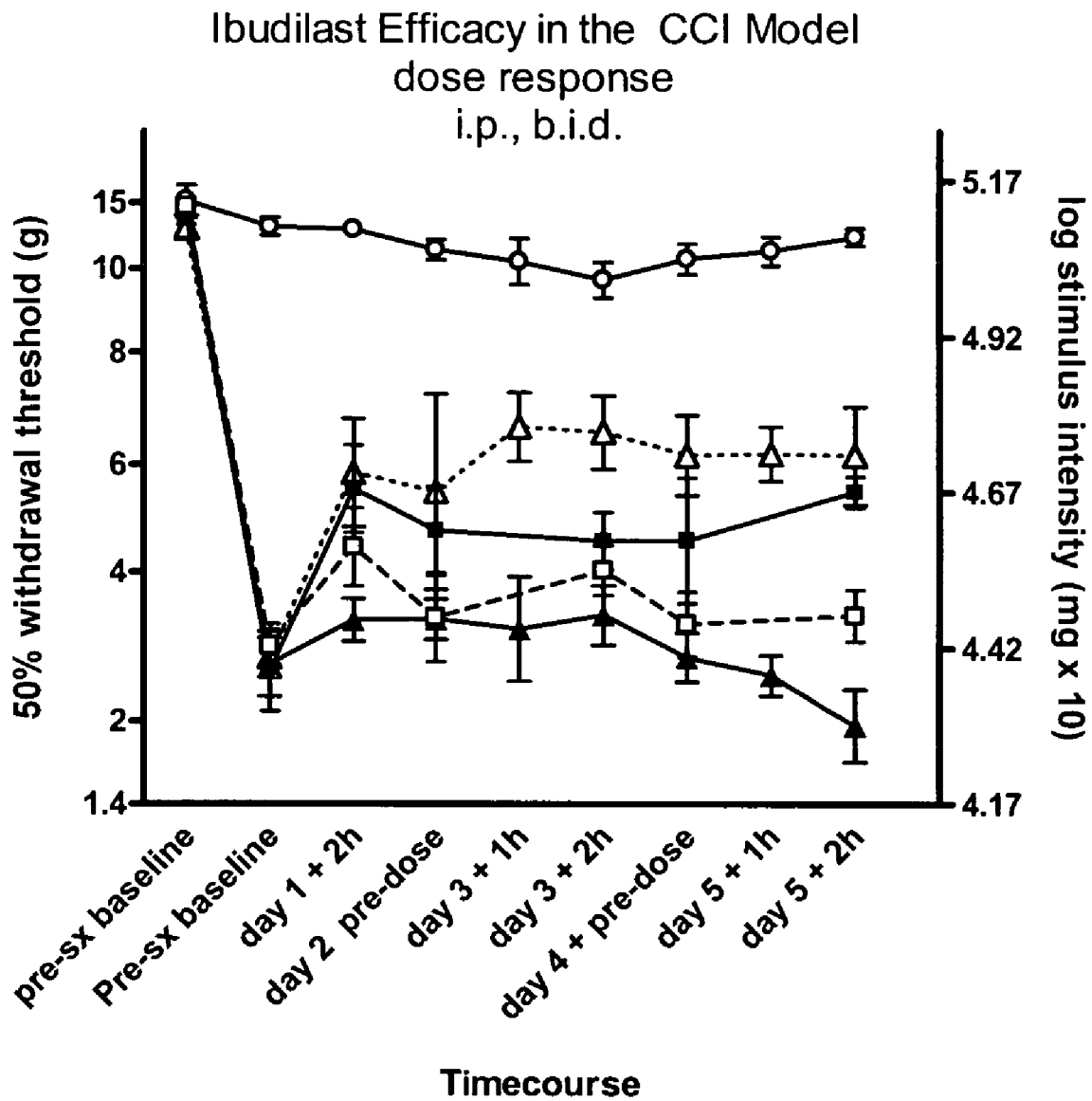
FIG. 1 presents a time course and dose response for attenuation of mechanical allodynia by intraperitoneal (i.p.) administration of ibudilast twice daily in a rat chronic constriction injury (CCI) model of neuropathic pain as described in Example 1. Pain is indicated by 50% withdrawal threshold as assessed by von Frey fibers. Data points represent the mean+/−standard error. Sham with 35% PEG/saline (-○-); CCI with 35% PEG400/saline (-▲-); CCI with 10 mg/kg ibudilast (...Δ...); CCI with 7.5 mg/kg ibudilast (-■-); CCI with 2.5 mg/kg ibudilast (-□-). n=4/group in sham and ≧5/group for CCIs. *=p<0.05 from vehicle control by Students t test.

The practice of the present invention will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20th Ed.; *Goodman & Gilman The Pharmacological Basis of Therapeutics*, J. Griffith Hardman, L. L. Limbird, A. Gilman, 10th Ed.

All publications, patents and patent applications cited herein, whether supra or infra, are hereby incorporated by reference in their entirety.

Definitions

Before describing the present invention in detail, it is to be understood that this invention is not limited to particular administration modes, patient populations, and the like, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present invention, the following terminology will be used in accordance with the definitions described below.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

By "pathological pain" is meant any pain resulting from a pathology, such as from functional disturbances and/or pathological changes, lesions, burns and the like. One form of pathological pain is "neuropathic pain" which is pain thought to initially result from nerve damage but extended or exacerbated by other mechanisms including glial cell activation. Examples of pathological pain include, but are not limited to, thermal or mechanical hyperalgesia, thermal or mechanical allodynia, diabetic pain, pain arising from irritable bowel or other internal organ disorders, endometriosis pain, phantom limb pain, complex regional pain syndromes, fibromyalgia, low back pain, cancer pain, pain arising from infection, inflammation or trauma to peripheral nerves or the central nervous system, multiple sclerosis pain, entrapment pain, and the like.

"Hyperalgesia" means an abnormally increased pain sense, such as pain that results from an excessive sensitiveness or sensitivity. Examples of hyperalgesia include but are not limited to cold or heat hyperalgesia.

"Hypalgesia" (or "hypoalgesia") means the decreased pain sense.

"Allodynia" means pain that results from normally non-noxious stimulus to the skin or body surface. Examples of allodynia include, but are not limited to, cold or heat allodynia, tactile or mechanical allodynia, and the like.

"Nociception" is defined herein as pain sense. "Nociceptor" herein refers to a structure that mediates nociception. The nociception may be the result of a physical stimulus, such as, mechanical, electrical, thermal, or a chemical stimulus. Nociceptors are present in virtually all tissues of the body.

"Analgesia" is defined herein as the relief of pain without the loss of consciousness. An "analgesic" is an agent or drug useful for relieving pain, again, without the loss of consciousness.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces and the like.

"Glial cells" refer to various cells of the CNS also known as microglia, astrocytes, and oligodendrocytes.

The terms "subject", "individual" or "patient" are used interchangeably herein and refer to a vertebrate, preferably a mammal. Mammals include, but are not limited to, murines, rodents, simians, humans, farm animals, sport animals and pets.

The terms "pharmacologically effective amount" or "therapeutically effective amount" of a composition or agent, as provided herein, refer to a nontoxic but sufficient amount of the composition or agent to provide the desired response, such as a reduction or reversal of neuropathic pain. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about", particularly in reference to a given quantity, is meant to encompass deviations of plus or minus five percent.

"Treatment" or "treating" neuropathic pain includes: (1) preventing pain, i.e. causing pain not to develop or to occur with less intensity in a subject that may be exposed to or predisposed to pain but does not yet experience or display pain, (2) inhibiting pain, i.e., arresting the development or reversing pain, or (3) relieving pain, i.e., decreasing the amount of pain experienced by the subject.

By "treating existing pain" is meant attenuating, elieving or reversing neuropathic pain in a subject that has been experiencing pain for at least 24 hours, such as for 24-96 hours or more, such as 25 . . . 30 . . . 35 . . . 40 . . . 45 . . . 48 . . . 50 . . . 55 . . . 65 . . . 72 . . . 80 . . . 90 . . . 96 . . . 100, etc. hours. The term also intends treating pain that has been occurring long-term, such as for weeks, months or even years.

Methods for Treating Neuropathic Pain

As described previously, the inventors have discovered ibudilast to be surprisingly effective in the treatment of neuropathic pain, e.g., neuropathic pain associated with certain syndromes such as viral neuralgias (e.g., herpes, AIDS), diabetic neuropathy, phantom limb pain, stump/neuroma pain, post-ischemic pain (stroke), fibromyalgia, reflex sympathetic dystrophy (RSD), complex regional pain syndrome (CRPS), cancer pain, vertebral disk rupture, and trigeminal neuralgia, cancer-chemotherapy-induced neuropathic pain, among others. Based upon results using standard pain models as described herein, the inventors have found the administration of ibudilast, which can be administered by various means and as infrequently as once daily, to be surprisingly effective in providing a measurable reduction in the severity of neuropathic pain, and in particular, in providing a measurable reduction in the severity if not reversal of certain types of neuropathic pain such as mechanical allodynia. Additional features of the invention are described herein.

Ibudilast

The methods of the invention for the treatment of neuropathic pain are based upon administration of the molecule, ibudilast. Ibudilast is a small molecule drug (molecular weight of 230.3) having the structure shown below.

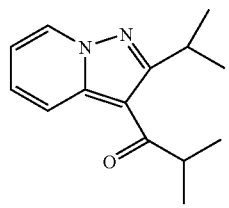

I

Ibudilast is also found under ChemBank ID 3227, CAS # 50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl)pyrazolo(1,5-a)pyridin-3-yl) 1-propanone; 3-isobutyryl-2-isopropylpyrazolo(1,5-a)pyridine]; and 1-(2-isopropyl-pyrazolo[1,5-a]pyridin-3-yl)-2-methyl-propan-1-one. Other synonyms for ibudilast include Ibudilastum (Latin), BRN 0656579, KC-404, MN-166. Its brand name is Ketas®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is a non-selective nucleotide phosphodiesterase (PDE) inhibitor (most active against PDE-3 and PDE-4), and has also been reported to have LTD4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca^{2+}$/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g. glial cells) resulting in the suppression of both pro-inflammatory mediator and neuroactive mediator release. References related to the foregoing include the following: Obernolte, R., et al. (1993) "The cDNA of a human lymphocyte cyclic-AMP phosphodiesterase (PDE IV) reveals a multigene family" *Gene* 129: 239-247; Rile, G., et al. (2001) "Potentiation of ibudilast inhibition of platelet aggregation in the presence of endothelial cells" *Thromb. Res.* 102: 239-246; Souness, J. E., et al. (1994) "Possible role of cyclic AMP phosphodiesterases in the actions of ibudilast on eosinophil thromboxane generation and airways smooth muscle tone" *Br. J. Pharmacol.* 111: 1081-1088; Suzumura, A., et al. (1999) "Ibudilast suppresses TNFα production by glial cells functioning mainly as type III phosphodiesterase inhibitor in CNS" *Brain Res.* 837: 203-212; Takuma, K., et al. (2001) "Ibudilast attenuates astrocyte apoptosis via cyclic GMP signaling pathway in an in vitro reperfusion model" *Br. J. Pharmacol.* 133: 841-848.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Method of Administration

As set forth above, the present invention is directed to a method of treating a mammalian subject suffering from neuropathic pain by administering a therapeutically effective dosage of ibudilast. Such administering is effective to decrease the amount of neuropathic pain experienced by the subject, i.e., to result in a significant attenuation or even reversal of neuropathic pain, as demonstrated in the accompanying Examples. Ibudilast is preferably administered at an initial dosage level effective to achieve a maximal plasma concentration (Cmax) of at least about 100 ng/ml, 125 ng/ml, 150 ng/ml, 175 ng/ml, 200 ng/ml, 225 ng/ml, 250 ng/ml, or 300 ng/ml or greater. In a preferred embodiment, ibudilast is administered at a dosage level effective to achieve a Cmax of at least about 125 ng/ml. Even more preferably, an initial therapeutic dosage of ibudilast correlating with detectable efficacy is one associated with a Cmax of at least about 350, 400, 450, 500, 550, 600, 650, 700, 750, 800, 850, 900, 950, 1000, 1100, 1200, 1300, 1400, 1500, 1600, 1700 or 1800 ng/ml or greater.

The method of the invention may, in certain instances, comprise a step of selecting a subject experiencing neuropathic pain prior to administering ibudilast thereto. Such subjects are typically selected from those suffering from postherpatic neuralgia, trigeminal neuralgia, and neuropathic pain associated with a condition selected from the group consisting of herpes, HIV, traumatic nerve injury, stroke, post-ischemia, fibromyalgia, reflex sympathetic dystrophy, complex regional pain syndrome, spinal cord injury, phantom limb pain, multiple-sclerosis, sciatica, and cancer or cancer-chemotherapeutic-induced neuropathic pain. In certain instances, the neuropathic pain subject selected is one whose native insulin production is non-impaired (i.e., is non-diabetic).

As can be seen from the accompanying Examples, the method of the invention is effective to not only significantly attenuate neuropathic pain, for example, mechanical allodynia, but to even reverse it. Soon after initial dosing, the administration of therapeutically effective levels of ibudilast demonstrated sustained efficacy—such that pain relief was long-lasting. Thus, in contrast to many other neuropathic pain medications currently on the market, administering of ibudilast is effective to result in sustained attenuation of neuropathic pain for an overnight duration. For example, a therapeutically effective dose of ibudilast is effective to treat neuropathic pain for a duration of up to at least 4 hours, 6 hours, 8 hours, 10 hours, 12 hours, 16 hours, 18 hours or even 20 hours or greater. This once daily oral efficacy observed in animals, which is expected to translate to humans based on pharmacokinetic projections of a sustained release form of ibudilast, would not be expected given the recommended frequencies (BID or TID) for ibudilast in existing clinical indications.

Ibudilast may also be administered in combination with an additional agent effective for treating neuropathic pain. In a preferred embodiment, such agent possesses a mechanism of action different from ibudilast. Exemplary agents include gabapentin, memantine, pregabalin, morphine and related opiates, cannabinoids, tramadol, lamotrigine, lidocaine, carbamazepine, duloxetine, milnacipran, and tricyclic antidepressants. As noted in Example 1, the administration of ibudilast in combination with the exemplary pain medication, morphine, did not adversely affect the opiate neuropathic pain efficacy of morphine, nor did the co-administration of morphine adversely impact the efficacy of ibudilast. The combination therapy resulted in a therapeutic efficacy that was greater than that demonstrated by either agent when administered alone.

Ibudilast is also effective in not only attenuating cancer-chemotherapeutic agent-induced neuropathy, but can also prevent the development of such neuropathy, as shown in Example 3. Examples of chemotherapeutic agents known to result in patient neuropathy include taxol, vinblastine, and vincristine. Administration of ibudilast is effective in attenuating or reversing neuropathic pain associated with the administration of such agents for the treatment of cancer.

Yet another advantage of the invention is the administration of a therapeutically effective dosage of ibudilast for treating neuropathic pain which surprisingly substantially avoids related emesis in the subject, as might have been expected based upon the therapeutic dosages administered. Accordingly, in one embodiment of the invention, administration of ibudilast is not accompanied by administration of an anti-emetic agent. That is to say, based upon the animal models, it is expected that in certain instances, efficacy is observed with a dosing regimen in humans that does not result in emesis, or that causes emesis initially (i.e., the first few times that ibudilast is administered), however, following such an initial dosing period (lasting, 1, 2, 3, 4, or 5 days), emesis no longer becomes an issue.

The method of the invention offers an additional advantage over existing neuropathic pain therapies, since existing neuropathic pain medications have sedation as a major side-effect, while ibudilast does not.

Preferred methods of delivery of ibudilast-based therapeutic formulations for the treatment of neuropathic pain include systemic and localized delivery, i.e., directly into the central nervous system. Such routes of administration include but are not limited to, oral, intra-arterial, intrathecal, intraspinal, intramuscular, intraperitoneal, intravenous, intranasal, and inhalation routes.

More particularly, an ibudilast-based formulation of the present invention may be administered for therapy by any suitable route, including without limitation, oral, rectal, nasal, topical (including transdermal, aerosol, buccal and sublingual), vaginal, parenteral (including subcutaneous, intramuscular, intravenous and intradermal), intrathecal, and pulmonary. The preferred route will, of course, vary with the condition and age of the recipient, the particular neuralgia-associated syndrome being treated, and the specific combination of drugs employed.

One preferred mode of administration for delivery of ibudilast is directly to neural tissue such as peripheral nerves, the retina, dorsal root ganglia, neuromuscular junction, as well as the CNS, e.g., to target spinal cord glial cells by injection into, e.g., the ventricular region, as well as to the striatum (e.g., the caudate nucleus or putamen of the striatum), spinal cord and neuromuscular junction, with a needle, catheter or related device, using neurosurgical techniques known in the art, such as by stereotactic injection (see, e.g., Stein et al., *J Virol* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000).

A particularly preferred method for targeting spinal cord glia is by intrathecal delivery, rather than into the cord tissue itself.

Another preferred method for administering the ibudilast-based compositions of the invention is by delivery to dorsal root ganglia (DRG) neurons, e.g., by injection into the epidural space with subsequent diffusion to DRG. For example, an ibudilast-based composition can be delivered via intrathecal cannulation under conditions where ibudilast is diffused to DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a convection-enhanced delivery (CED) system. In this way, ibudilast can be delivered to many cells over large areas of the CNS. Any convection-enhanced delivery device may be appropriate for delivery of ibudilast. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, an ibudilast-based composition of the invention is delivered via CED devices as follows. A catheter, cannula or other injection device is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target. For a detailed description regarding CED delivery, see U.S. Pat. No. 6,309,634, incorporated herein by reference in its entirety.

An ibudilast composition of the invention, when comprising more than one active agent, may be administered as a single combination composition comprising a combination of ibudilast and at least one additional active agent effective in the treatment of neuropathic pain. In terms of patient compliance and ease of administration, such an approach is preferred, since patients are often adverse to taking multiple pills or dosage forms, often multiple times daily, over the duration of treatment. Alternatively, albeit less preferably, the combination of the invention is administered as separate dosage forms. In instances in which the drugs comprising the therapeutic composition of the invention are administered as separate dosage forms and co-administration is required, ibudilast and each of the additional active agents may be administered simultaneously, sequentially in any order, or separately.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast will range from a total daily dosage of about 0.1 and 200 mg/day, more preferably, in an amount between 1-200 mg/day, 30-200 mg/day, 1-100 mg/day, 30-100 mg/day, 30-300 mg/day, 1-60 mg/day, 1-40 mg/day, or 1-10 mg/day, administered as either a single dosage or as multiple dosages. Preferred dosage amounts include dosages greater than about 10 mg BID or TID. That is to say, a preferred dosage amount is greater than about 20 mg/day or greater than 30 mg/day. Dosage amounts may be selected from 30 mg/day, 40 mg/day, 50 mg/day, 60 mg/day, 70 mg/day, 80 mg/day, 90 mg/day or 100 mg/day or more. Depending upon the dosage amount and precise condition to be treated, administration can be one, two, or three times daily for a time course of one day to several days, weeks, months, and even years, and may even be for the life of the patient. Illustrative dosing regimes will last a period of at least about a week, from about 1-4 weeks, from 1-3 months, from 1-6 months, from 1-50 weeks, from 1-12 months, or longer.

Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Approaches for Treatment of Neuropathic Pain

Current pain therapies primarily target the neurons that relay pain signals. These neurons are part of a long-described and evolutionarily conserved pathway in vertebrates that transmits signals from the periphery to the somatosensory cortex. A growing body of literature suggests that neurons are not exclusive entities in the development of persistent painful states (Watkins and Maier (2003) *Nat. Rev. Drug Discov.* 2:973-85). Glial cells (microglia and astrocytes) have been established as key participants of neuropathic pain in well-established animal models (Wieseler-Frank et al. (2004) *Neurochem. Int.* 45:389-95), and have been implicated in human pathogenesis as well (Watkins and Maier (2002) *Physiol Rev.* 82: 981-1011).

Several cues activate glia such as immune challenges, infection and/or peripheral inflammation, and substances released during prolonged neuron-to-neuron transmission (e.g., neurotransmitters, substance P, fractalkine, etc.). Glial function is changed dramatically upon activation, resulting in elevated release of neuroactive substances. In so doing, they also increase the gain of neural transmission, amplifying the afferent signals and hence exacerbating pain sensation.

Experimental evidence has demonstrated that glia activation and subsequent events play a critical role in pain facilitation in experimental animals. For example: (i) administration of pro-inflammatory glial-activating cytokines such as interleukin-1β (IL-1β) or tissue necrosis factor α (TNFα) exacerbate underlying neuropathies; (ii) pharmacological blockade of glial activation blocks and/or reverses pain facilitation in every animal model examined; (iii) pain facilitation can be blocked and/or reversed by the antagonism of the neuroactive substances released by activated glia; (iv) pain responses in normal animals are not affected by either the blockade of glial activation or the antagonism of their pro-inflammatory products; and (v) glial cells also release other neuroactive substances including pro-inflammatory cytokines, excitatory amino acids, and prostaglandins which can amplify neuropathic pain.

Ibudilast is a potent suppressor of glial activation (Mizuno et al. (2004) *Neuropharmacology* 46: 404-411). In a dose-dependent manner, ibudilast has been shown to suppress the production of nitric oxide (NO), reactive oxygen species, interleukin (IL)-1β, IL-6, and tumor necrosis factor (TNF) and enhance the production of the inhibitory cytokine, IL-10, along with additional neurotrophic factors including nerve growth factor (NGF), glia-derived neurotrophic factor (GDNF), and neurotrophin (NT)-4 in activated microglia. Thus, ibudilast-mediated-neuroprotection was found to be primarily due to the inhibition of inflammatory mediators and the upregulation of neurotrophic factors.

Ibudilast crosses the blood-brain barrier when administered systemically (Sugiyama et al. (1993) *No To Shinkei* 45(2):139-42; FIG. 5), thus eliminating the need for more invasive methods of administration in order to access central sites of inflammation involved in neuropathic pain pathogenesis. Other known compounds capable of attenuating glial activation include fluorocitrate and minocycline, and they have shown efficacy in rodent models of neuropathic pain. However, each is unacceptable for human therapy. Fluorocitrate is unsuitable for human administration because it can block glial uptake of excitatory amino acids (Berg-Johnsen et al. (1993) *Exp. Brain Res.* 96(2):241-6), an essential function of glia in the maintenance of normal CNS homeostasis. Minocycline, while potentially useful in preventing glial activation, does not appear to reverse extant glial pain facilitation (Raghavendra et al. (2003) *J. Pharmacol. and Exp. Therapeutics* 306: 624-630). Hence, this discovery of ibudilast efficacy for neuropathic pain following systemic administration with well-tolerated dose levels represents a unique therapy.

Taken together, glia and their pro-inflammatory products may present opportunities for new strategies for pain control. Of the substances released by activated glia, pro-inflammatory cytokines (especially IL-10 and TNFα) are critical for this type of pain facilitation. Thus, in accordance with yet another embodiment of the invention, administration of ibudilast is effective to block the release of pro-inflammatory cytokines.

Pain Models

The ability of ibudilast to treat neuropathic pain can be evaluated by any of the standard pain models known in the art. Examples of such models are as follows.

Carrageenan-induced Paw Hyperalgesia Model: The carrageenan paw hyperalgesia test is a model of inflammatory pain. A subcutaneous injection of carrageenan is made into the left hindpaws of rats. The rats are treated with a selected agent before, e.g., 30 minutes, the carrageenan injection or after, e.g., two hours after, the carrageenan injection. Paw pressure sensitivity for each animal is tested with an analgesymeter three hours after the carrageenan injection. See, Randall et al., *Arch. Int. Pharmacodyn.* (1957) 111:409-419.

The effects of selected agents on carrageenan-induced paw edema can also be examined. This test (see, Vinegar et al., *J. Phamacol. Exp. Ther*. (1969) 166:96-103) allows an assessment of the ability of a compound to reverse or prevent the formation of edema evoked by paw carrageenan injection. The paw edema test is carried out using a plethysmometer for paw measurements. After administration of a selected agent, a carrageenan solution is injected subcutaneously into the lateral foot pad on the plantar surface of the left hind paw. At three hours post-carrageenan treatment, the volume of the treated paw (left) and the un-treated paw (right) is measured using a plethysmometer.

Von frey Filament Test: The effect of compounds on mechanical allodynia can be determined by the von Frey filament test in rats with a tight ligation of the L-5 spinal nerve: a model of painful peripheral neuropathy. The surgical procedure is performed as described by Kim et al., *Pain* (1992) 50:355-363. A calibrated series of von Frey filaments are used to assess mechanical allodynia (Chaplan et al., *J. Neurosci. Methods* (1994) 53:55-63). Filaments of increasing stiffness are applied perpendicular to the midplantar surface in the sciatic nerve distribution of the left hindpaw. The filaments are slowly depressed until bending occurred and are then held for 4-6 seconds. The filament application order and number of trials were determined by the up-down method of Dixon (Chaplan et al., supra). Flinching and licking of the paw and paw withdrawal on the ligated side are considered positive responses.

Chronic Constriction Injury: Heat and cold allodynia responses as well as mechanical allodynia sensations can be evaluated as described below in rats having a chronic constriction injury (CCI). A unilateral mononeuropathy is produced in rats using the chronic constriction injury model described in Bennett et al., *Pain* (1988) 33:87-107. CCI is produced in anesthetized rats as follows. The lateral aspect of each rat's hind limb is shaved and scrubbed with Nolvasan. Using aseptic techniques, an incision is made on the lateral aspect of the hind limb at the mid-thigh level. The biceps femoris is bluntly dissected to expose the sciatic nerve. On the right hind limb of each rat, four loosely tied ligatures (for example, Chromic gut 4.0; Ethicon, Johnson and Johnson, Somerville, N.J.) are made around the sciatic nerve approximately 1-2 mm apart. On the left side of each rat, an identical dissection is performed except that the sciatic nerve is not ligated (sham). The muscle is closed with a continuous suture pattern with, e.g., 4-0 Vicryl (Johnson and Johnson, Somerville, N.J.) and the overlying skin is closed with wound clips. The rats are ear-tagged for identification purposes and returned to animal housing.

Chung Model of Rat Neuropathic Pain: Heat and cold allodynia responses as well as mechanical allodynia sensations can be evaluated as described below in rats following spinal nerve injury (e.g. ligation, transaction). Details are as initially described in S H Kim and J M Chung, *Pain* (1992) 50:355-363.

The Hargreaves Test: The Hargreaves test (Hargreaves et al., *Pain* (1998) 32:77-88) is also a radiant heat model for pain. CCI rats are tested for thermal hyperalgesia at least 10 days post-op. The test apparatus consists of an elevated heated (80-82° F.) glass platform. Eight rats at a time, representing all testing groups, are confined individually in inverted plastic cages on the glass floor of the platform at least 15 minutes before testing. A radiant heat source placed underneath the glass is aimed at the plantar hind paw of each rat. The application of heat is continued until the paw is withdrawn (withdrawal latency) or the time elapsed is 20 seconds. This trial is also applied to the sham operated leg. Two to four trials are conducted on each paw, alternately, with at least 5 minutes interval between trials. The average of these values represents the withdrawal latency.

Cold Allodynia Model: The test apparatus and methods of behavioral testing is described in Gogas et al., *Analgesia* (1997) 3:111-118. The apparatus for testing cold allodynia in neuropathic (CCI) rats consists of a Plexiglass chamber with a metal plate 6 cm from the bottom of the chamber. The chamber is filled with ice and water to a depth of 2.5 cm above the metal plate, with the temperature of the bath maintained at 0-4° C. throughout the test. Each rat is placed into the chamber individually, a timer started, and the animal's response latency was measured to the nearest tenth of a second. A "response" is defined as a rapid withdrawal of the right ligated hindpaw completely out of the water when the animal is stationary and not pivoting. An exaggerated limp while the animal is walking and turning is not scored as a response. The animals' baseline scores for withdrawal of the ligated leg from the water typically range from 7-13 seconds. The maximum immersion time is 20 seconds with a 20-minute interval between trials.

Additional information regarding models of neuropathic pain is available in the following publications. Bennett G J, Xie Y K (1988) "A peripheral mononeuropathy in rat that produces disorders of pain sensation like those seen in man" *Pain* 33: 87-107; Chaplan S R, Bach F W, Pogrel J W, Chung J M, Yaksh T L (1994) "Quantitative assessment of tactile allodynia in the rat paw" *J. Neurosci. Meth*. 53: 55-63; Fox A, Gentry C, Patel S, Kesingland A, Bevan S (2003) "Comparative activity of the anti-convulsants oxcarbazepine, carbamazepine, lamotrigin and gabapentin in a model of neuropathic pain in the rat and guinea-pig" *Pain* 105: 355-362; Milligan E D, Mehmert K K, Hinde J L, Harvey L O J, Martin D, Tracey K J, Maier S F, Watkins L R (2000) "Thermal hyperalgesia and mechanical allodynia produced by intrathecal administration of the Human Immunodeficiency Virus-1 (HIV-1) envelope glycoprotein, gp120" *Brain Res*. 861: 105-116; De Vry J, Kuhl E, Franken-Kunkel P, Eckel G (2004) "Pharmacological characterization of the chronic constriction injury model of neuropathic pain" *Eur. J. Pharmacol*. 491:137-148. Polomano R C, Mannes A J, Clark U S, Bennett G J (2001) "A painful peripheral neuropathy in the rat produced by the chemotherapeutic drug, paclitaxel" *Pain* 94:293-304.

Formulations of the Invention

In addition to comprising ibudilast, a therapeutic formulation of the invention may optionally contain one or more additional components as described below.

Excipients/Carriers

In addition to ibudilast, the compositions of the invention for treating neuropathic pain may further comprise one or more pharmaceutically acceptable excipients or carriers. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the invention may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the invention are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

An ibudilast-containing composition of the invention may also include an antimicrobial agent, e.g., for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition of the invention may also contain one or more antioxidants. Antioxidants are used to prevent oxidation, thereby preventing the deterioration of the drug(s) or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the invention may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an ibudilast composition of the invention is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

Other Actives

A formulation (or kit) in accordance with the invention may contain, in addition to ibudilast, one or more additional active agents effective in treating neuropathic pain. Preferably, the active agent is one that possesses a mechanism of action different from that of ibudilast. Such actives include gabapentin, memantine, pregabalin, morphine and related opiates, cannabinoids, tramadol, lamotrigine, carbamazepine, duloxetine, milnacipran, and tricyclic antidepressants.

Gabapentin, also known as Neurontin®, is structurally related to the neurotransmitter GABA. Although structurally related to GABA, gabapentin does not interact with GABA receptors, is not converted metabolically into GABA or a GABA agonist, and is not an inhibitor of GABA uptake or degradation. Gabapentin has no activity at GABAA or GABAB receptors of GABA uptake carriers of the brain, but instead interacts with a high-affinity binding site in brain membranes (an auxiliary subunit of voltage-sensitive $Ca^{2+}$ channels). The exact mechanism of action is unknown, only that its physiological site of action is the brain. The structure of gabapentin allows it to pass freely through the blood-brain barrier. In vitro, gabapentin has many pharmacological actions including modulating the action of the GABA synthetic enzyme, increasing non-synaptic GABA responses from neural tissue, and reduction of the release of several mono-amine neurotransmitters. Daily dosages of gabapentin typically range from about 600 to 2400 mg/day, more preferably from about 900 to 1800 mg/day, and are administered in divided doses, for example, three times a day. Conventional unit dosage forms are 300 or 400 mg capsules or 600 or 800 mg tablets.

The active agent, memantine, is a receptor antagonist. Memantine is believed to function as a low to moderate affinity uncompetitive (open-channel) NMDA receptor antagonist which binds to the NMDA receptor-operated cation channels. Recommended daily dosage amounts typically range from about 5 mg to 20 mg.

The opiate, morphine, elicits its effects by activating opiate receptors that are widely distributed throughout the brain and body. Once an opiate reaches the brain, it quickly activates the opiate receptors found in many brain regions and produces an effect that correlates with the area of the brain involved. There are several types of opiate receptors, including the delta, mu, and kappa receptors. Opiates and endorphins function to block pain signals by binding to the mu receptor site.

The cannabinoids, e.g., tetrahydrocannabinol, bind to the cannabinoid receptor referred to as $CB_1$. $CB_1$ receptors are found in brain and peripheral tissues; $CB_1$ receptors are present in high quantities in the central nervous system, exceeding the levels of almost all neurotransmitter receptors. An additional cannabinoid receptor subtype termed 'CB2' has also been identified. See, e.g., Martin, B. R., et al., *The Journal of Supportive Oncology*, Vol. 2, Number 4, July/August 2004.

Although its mechanism of action has not yet been fully elucidated, the opioid, tramadol, is believed to work through modulation of the GABAergic, noradrenergic and serotonergic systems. Tramadol, and its metabolite, known as M1, have been found to bind to μ-opioid receptors (thus exerting its effect on GABAergic transmission), and to inhibit re-uptake of 5-HT and noradrenaline. The second mechanism is believed to contribute since the analgesic effects of tramadol are not fully antagonised by the μ-opioid receptor antagonist naloxone. Typical daily dosages range from about 50 to 100 milligrams every 4 to 6 hours, with a total daily dosage not to exceed 400 milligrams.

Lamotrigine is a phenyltriazine that stabilizes neuronal membranes by blocking voltage-sensitive sodium channels, which inhibit glutamate and aspartate (excitatory amino acid neurotransmitter) release. The daily dosage of lamotrigine typically ranges from 25 milligrams per day to 500 mg per day. Typical daily dosage amounts include 50 mg per day, 100 mg per day, 150 mg per day, 200 mg per day, 300 mg per day, and 500 mgs per day, not exceed 700 mgs per day.

Carbamazepine acts by blocking voltage-sensitive sodium channels. Typical adult dosage amounts range from 100-200 milligrams one or two times daily, to an increased dosage of 800-1200 milligrams daily generally administered in 2-3 divided doses.

Duloxetine is a potent inhibitor of neuronal uptake of serotonin and norepinephrine and a weak inhibitor of dopamine re-uptake. Typical daily dosage amounts range from about 40 to 60 milligrams once daily, or 20 to 30 milligrams twice daily.

Milnacipran acts as a serotonin and norepinephrine reuptake inhibitor. Daily dosage amounts typically range from about 50 to 100 milligrams once or twice daily.

The dosage amounts provided above are meant to be merely guidelines; the precise amount of a secondary active agent to be administered during combination therapy with ibudilast will, of course, be adjusted accordingly and will depend upon factors such as intended patient population, the particular neuropathic pain symptom or condition to be treated, potential synergies between the active agents administered, and the like, and will readily be determined by one skilled in the art based upon the guidance provided herein.

Sustained Delivery Formulations

Preferably, the compositions are formulated in order to improve stability and extend the half-life of ibudilast. For example, ibudilast may be delivered in a sustained-release formulation. Controlled or sustained-release formulations are prepared by incorporating ibudilast into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

Delivery Forms

The ibudilast compositions described herein encompass all types of formulations, and in particular, those that are suited for systemic or intrathecal administration. Oral dosage forms include tablets, lozenges, capsules, syrups, oral suspensions, emulsions, granules, and pellets. Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast composition of the invention is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx™ (Aradigm), the Ultravent® (Mallinkrodt), and the Acorn II® (Marquest Medical Products). A composition of the invention may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the invention are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the invention may also be a sustained release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the invention may optionally include other agents conventional in the pharmaceutical arts and particular type of formulation being employed, for example, for oral administration forms, the composition for oral adminsitration may also include additional agents as sweeteners, thickeners or flavoring agents.

The compositions of the present invention may also be prepared in a form suitable for veterinary applications.

Kits

Also provided herein is a kit containing at least one combination composition of the invention, accompanied by instructions for use.

For example, in instances in which each of the drugs themselves are administered as individual or separate dosage forms, the kit comprises ibudilast in addition to each of the drugs making up the composition of the invention, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and gabapentin, the kit may be organized by any appropriate time period, such as by day. As an example, for Day 1, a representative kit may comprise unit dosages of each of ibudilast and gabapentin. If each of the drugs is to be administered twice daily, then the kit may contain, corresponding to Day 1, two rows of unit dosage forms of each of ibudilast and gabapentin, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister paks, dessicants, and the like.

It is to be understood that while the invention has been described in conjunction with preferred specific embodiments, the foregoing description as well as the examples that follow are intended to illustrate and not limit the scope of the invention. Other aspects, advantages and modifications within the scope of the invention will be apparent to those skilled in the art to which the invention pertains.

EXAMPLES

Example 1

Effect of Ibudilast on Mechanical Allodynia in a Rat CCI Model of Neuropathic Pain The effect of ibudilast on mechanical allodynia was assessed in a rat chronic constriction injury (CCI) model of neuropathic pain.

Methods.

Test Agents: Ibudilast was obtained as pure powder from Sigma (St. Louis, Mo.) or Haorui Pharma (Edison, N.J.). It was prepared daily as a solution for intraperitoneal (i.p.) administration. An appropriate amount of ibudilast was dissolved in 100% polyethylene glycol (PEG) 400 (Sigma) and then diluted down to a final concentration of 35% PEG400 in sterile saline (0.9% for injection).

Test Article Administration: Ibudilast was administered at 2.5 mg/kg (0.9 ml/kg of 2.8 mg/ml in 35% PEG/saline), 7.5 mg/kg (2.7 ml/kg of 2.8 mg/ml in 35% PEG/saline), or 10 mg/kg twice daily, (3.7 ml/kg of 2.7 mg/ml in 35% PEG/saline) each morning (typically 8 am) and pm (typically 3 pm). For oral efficacy studies, ibudilast was administered at 50 mg/kg formulated in a solution of 10% HCO-60, 10% PEG 400, saline, or could be administered at 21-25.5 mg/kg (7-8.5 ml/kg of 3 mg/ml in 35% PEG/saline) where attenuation of mechanical allodynia in rat CCI was also observed. Drug stability and concentration were validated by HPLC/MS/MS.

Animals: Pathogen-free adult male Sprague-Dawley rats (280-350 g; Harlan Labs) were used in all experiments. Rats were housed in temperature (23+/−3° C.) and light (12:12 light: dark; lights on at 0700 hr) controlled rooms with standard rodent chow and water available ad libitum. Behavioral testing was performed during the light cycle.

Chronic constriction injury (CCI): CCI was created at mid-thigh level of the right hind leg. Four sterile, absorbable surgical chromic gut sutures (cuticular 4-0, chromic gut, 27", cutting FS-2; Ethicon, Somerville, N.J.) were loosely tied around the gently isolated sciatic nerve under isoflurane anesthesia (Phoenix Pharm., St. Joseph, Mo.). The sciatic nerves of sham-operated rats were exposed but not ligated. Suture placements were typically verified at sacrifice by visual inspection. Randomization to various treatment groups and initiation of dosing occurred 7-8 days post-surgery.

Behavioral Measures von Frey Test: The von Frey test was performed within the sciatic or saphenous innervation area of the hindpaws. Briefly, a logarithmic series of 10 calibrated Semmes-Weinstein monofilaments (von Frey hairs; Stoelting, Wood Dale, Ill.) was applied randomly to the right hind paws to determine the stimulus intensity threshold stiffness required to elicit a paw withdrawal response. Log stiffness of the hairs is determined by $log_{10}$ (milligrams×10). The 10 stimuli had the following log-stiffness values (values in milligrams are given in parenthesis): 3.61 (407 mg), 3.84 (692 mg), 4.08 (1,202 mg), 4.17 (1,479 mg), 4.31 (2,041 mg), 4.56 (3,630 mg), 4.74 (5,495 mg), 4.93 (8,511 mg), 5.07 (11,749 mg), and 5.18 (15,136 mg). The range of monofilaments used in these experiments (0.407-15.136 gm) produces a logarithmically graded slope. Interpolated 50% response threshold data is expressed as stimulus intensity in $log_{10}$ (milligrams× 10) or as gram fiber force. Assessments were made prior to (baseline) and at specific times after intraperitoneal drug administration. Behavioral testers were blinded to treatment groups. Responses were used to calculate the 50% paw withdrawal threshold (absolute threshold), by fitting a Gaussian integral psychometric function using a maximum-likelihood fitting method and this fitting method allows parametric statistical analyses.

Studies and Results

Dose Selection Study: Preliminary studies were designed to assess rat tolerability to single and multiple intraperitoneal administrations of ibudilast. Ibudilast i.p. doses>20 mg/kg formulated in 35% PEG/saline administered at a volume</=5 ml/kg, produced adverse behavioral effects in the rats that lasted up to 1 hr in duration. These included extended head, increased respiratory rate, occasional circling behavior and vocalization, and lethargy. Rats treated with vehicle alone at the same dose volumes did not exhibit any adverse effects. In contrast, doses</=15 mg/kg ip were generally well tolerated.

Acute Efficacy Study: Initially, a small set of animals (n=3-4/group; groups=Sham controls, CCI vehicles, CCI ibudilast) were tested for an acute reduction in allodynia following a single i.p. administration of 10-15 mg/kg test agent. Mechanical allodynia was measured at baseline (just prior to dosing) and 1, 2, 4, and 16 hr post-administration. Relative to the CCI vehicle animals, the ibudilast-treated rats showed a reduction in allodynia. Allodynia is defined as a painful withdrawal response to a normally innocuous stimulus. This was apparent at +1 hr, maximum at +2 hr, and then returned to baseline at 16 hr (data not shown, but see also FIG. 1). Importantly, there were no changes in paw withdrawal thresholds in the ibudilast sham animals indicating that the neuropathic pain efficacy in the CCI rats was not due to overt anesthesia.

Multi-day Study for Neuropathic Pain Efficacy: Given the results of the preliminary acute study indicating transient efficacy, a 1 week study was undertaken wherein the animals (n=4/group for shams and 5-8/group for CCIs) were administered 2.5, 7.5, or 10 mg/kg ibudilast or 35% PEG/saline vehicle twice daily, i.p., and mechanical allodynia was monitored at various time intervals post-dosing. The +1 hr and +2 hr time points were obtained following the am dose. A pre-dose test was conducted each day ~16 hr after the pm dose on the previous day in order to assess durability of efficacy.

As shown in FIG. 1, ibudilast treatment attenuated the magnitude of allodynia in the CCI rats. Notably, reversal was biologically and statistically significant and consistently manifested at +2 hr post-administration. Moreover, within two days of this bid regiment, the effect was already becoming more sustained for doses>2.5 mg/kg, such that reversal of neuropathic pain was evident as long as 16 hr following ibudilast treatment. Such durable efficacy is uncommon for most neuropathic pain drugs, and would not necessarily be predicted from the pharmacokinetic profile.

Figure 6:
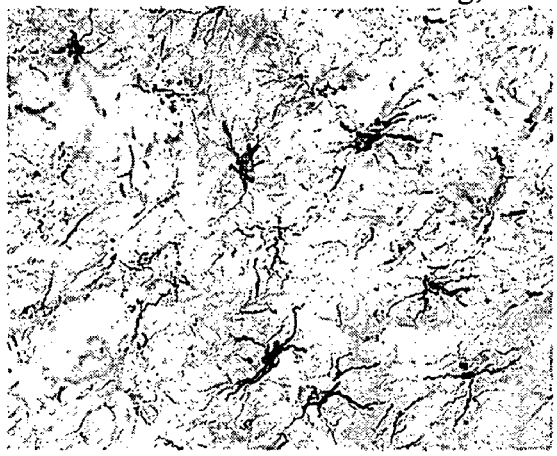
FIG. 6 presents GFAP immunohistochemistry of lumbar spinal cord sections from CCI vehicle control or ibudilast-treated rats. On the eighth day following CCI surgery, rats received ibudilast (7.5 mg/kg) or vehicle control (35% PEG400/saline) ip BID for 5 days. Slides depicted are representative of 4 animals analyzed for each treatment group at 40× magnification. Left side=vehicle control animal; Right side=ibudilast-treated.
Figure 6:
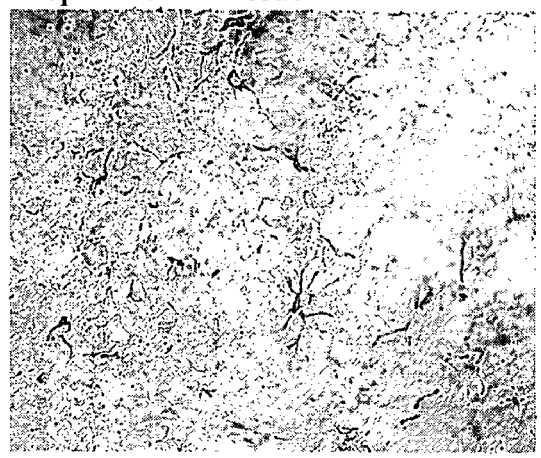

Study of Attenuation of Glial Cell Activation in Ibudilast-Treated CCI Rats: At the end of the 5-day study, animals (4/group) from the CCI vehicle control or CCI ibudilast group were euthanized and lumbar spinal cord tissue was isolated and stained for astrocyte activation with an antibody reactive against Glial Fibrillary Acidic Protein (GFAP) as described in B A Winkelstein and J A DeLeo, *Brain Research* (2002) 956:294-301. FIG. 6 depicts a typical staining profile from CCI vehicle-treated animals. Enlarged (activated) astrocytes, typically observed in subjects with neuropathic pain (CCI rats in this case), are visible in the CCI group. In contrast, a representative image from an ibudilast-treated rat, which demonstrates good attenuation of allodynia, is presented. Reduced glial cell activation as measured by GFAP staining is observed in the ibudilast-treated animal(s).

Oral Efficacy Study: A 5-day study was undertaken wherein animals (n=8/group) were administered 21 mg/kg ibudilast or 35% PEG/saline vehicle twice daily, p.o., for 2 days and then increased to 25.5 mg/kg ibudilast for an additional 3 days. Pre- and post mechanical allodynia testing was conducted at various time intervals on days 1, 3, and 5. The +1 hr and +2 hr time points were obtained following the am dose. A pre-dose test on these days was also conducted in order to assess durability of efficacy. Attenuation of allodynia was observed in ibudilast-treated animals as early as 4 hr after the first dose and became durable (lasting from pm dosing to next day's pre-am dosing test) following 2 days of treatment (data not shown).

Figure 2:
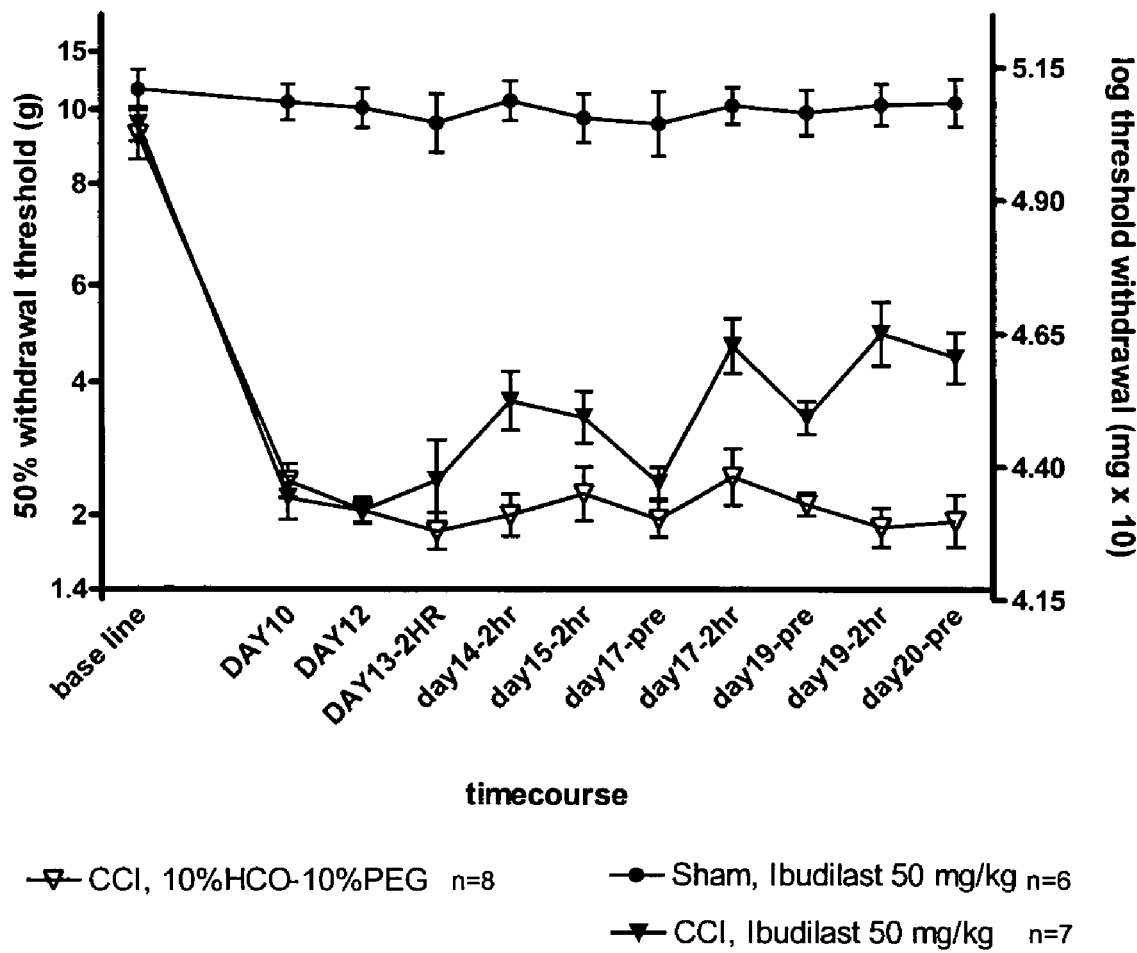
FIG. 2 presents a time course and dose response for attenuation of mechanical allodynia by oral ibudilast administration in a rat chronic constriction injury model of neuropathic pain as described in Example 1. Pain is indicated by 50% withdrawal threshold as assessed by von Frey fibers. Data points represent the mean+/−standard error. Sham with vehicle control (10% HCO-60, 10% PEG400, saline) (closed circle); CCI vehicle control (open triangle); CCI 50 mg/kg ibudilast (closed triangle). n≧5/group. *=p<0.05 from vehicle control by Students t test.

Efficacy in a 1 week study wherein ibudilast was administered to rats (n≧6/group) by oral gavage only once daily (approximately 9 am) was also assessed. The vehicle formulation was 10% HCO-60, 10% PEG400 in saline. As shown in FIG. 2, oral ibudilast administration significantly attenuated the magnitude of allodynia in the CCI rats following 2 days of dosing shortly after the morning dose and durable efficacy, lasting overnight, was observed within 7 days of dosing.

Pharmacokinetics. Plasma Ibudilast Concentrations Correlating with Efficacy: Dedicated pharmacokinetic studies in normal rats were performed with ibudilast dosing i.p. or p.o.

in order to correlate drug plasma levels with changes in mechanical allodynia (i.e. neuropathic pain efficacy). Following dosing (time t=0), serial bleeding from n=3 rats/time point and 6 time points interspersed between 5 min and 6 hr was obtained, plasma was isolated, and ibudilast concentrations were determined by a HPLC and two-dimensional mass spectrometry (LC/MS/MS) method (described in Example 4) sensitive to ≦1 ng/ml. Maximal plasma concentrations (Cmax) correlating with the first indications of allodynia efficacy following ibudilast i.p. treatment in CCI rats—i.e. 2.5 mg/kg—yielded maximal plasma concentrations averaging 125 ng/ml. Significant efficacy in neuropathic pain was observed at 7.5 mg/kg i.p. and correlated with maximal average plasma concentrations of 1714 ng/ml. When administered orally at 21 mg/kg in PEG400/saline or 50 mg/kg in 10% HCO-60/10% PEG400/saline, wherein clearly identifiable and statistically signifant efficacy was observed, the average maximal plasma concentrations were 325 ng/ml (FIG. 5B) or 387 ng/ml, respectively. Moreover, pharmacokinetic-pharmacodynamic analyses involving PK parameters including Cmax, area under the curve (AUC), and elimination half-life ($t_{1/2}$) indicated Cmax is an important parameter in establishing efficacy.

Combination Therapy Benefit with Morphine: A rat CCI efficacy study was performed wherein 7.5 mg/kg ibudilast in 35% PEG/saline administered ip bid was performed alone or in combination with 1 mg/kg morphine administered s.c. over several days of treatment. Reversal of allodynia in comparison to vehicle control by morphine was greater than that by ibudilast and the combination of morphine+ibudilast was better than either agent alone. (Data not shown). Hence, ibudilast treatment in combination does not interfere with opiate neuropathic pain efficacy, and vice versa, and combined therapy efficacy is enhanced relative to either agent alone. Similar results are expected with other neuropathic pain drugs including gabapentin, cymbalta, etc.

Conclusions

In a classic, validated model (rat CCI) of neuropathic pain wherein the primary efficacy endpoint was mechanical allodynia, ibudilast administration systemically (i.p. or p.o.) at daily frequency of once or twice daily markedly attenuated allodynia. Additionally, it has been determined that ibudilast can be combined with other neuropathic pain therapies such as morphine, where the resulting neuropathic pain efficacy observed for the combination is greater than that observed for either agent alone.

The plasma concentrations of systemically-administered ibudilast which correlated with neuropathic pain efficacy correlated with maximal plasma concentrations (Cmax)≧125 ng/ml, which is above the plasma concentrations typically observed in asthma or post-stroke patients treated with ibudilast. Recommended and most-practiced dosing regimens of ibudilast in humans are 10 mg BID or TID, which yields single dose Cmax of 25 ng/ml (Ketas® Package Insert) or multi-dose steady state Cmax of 45 ng/ml (Z Cai-Li et al., (2003) *Acta Pharmacol Sin* 4:342-343. Based on the data provided herein, it is expected that actual dose levels optimal for neuropathic pain utility in humans will require ibudilast (as dispensed as Ketas® and other commercial generic forms) dosage levels above 10 mg BID or TID.

By staining for GFAP immunoreactivity in spinal cord tissue from rats experiencing neuropathic pain (CCI procedure), it was shown that the astrocyte activation typically observed following nerve injury was reduced following systemic (i.p.) administration of ibudilast. Moreover, such reduction of GFAP immunoreactivity correlated with ibudilast efficacy for reducing mechanical allodynia.

Example 2

Effect of Ibudilast on Mechanical Allodynia in a Rat Chung Model of Neuropathic Pain The effect of ibudilast on mechanical allodynia in a rat Chung model of neuropathic pain was assessed.

Methods

Test Agents: Haorui and Sigma ibudilast was formulated as described above. Ibudilast was administered at 10 mg/kg twice daily, (3.7 ml/kg of 2.7 mg/ml in 35% PEG/saline) i.p. each morning (typically 8 am) and pm (typically 3 pm).

Animals: Pathogen-free adult male Wistar rats (150-200 g; Elevage Janvier) were used in all experiments. Rats were housed in temperature (23+/−3° C.) and light (12:12 light: dark; lights on at 0700 hr) controlled rooms with standard rodent chow and water available ad libitum. Behavioral testing was performed during the light cycle.

Chung model: Rats were anesthetized under isoflurane (4-5% induction and 2-3% maintenance in 100% oxygen) and an incision at the L4-S2 levels was performed to expose the left L5 and L6 spinal nerves. A ligature was tied tightly around each nerve. The wound was then sutured. The rats received an injection of clamoxil and were allowed to recover. Sham controls were subjected to the same surgical procedure except that the nerves were not ligated.

Behavioral Measures von Frey Test: The von Frey test was performed as described above for the CCI model.

Studies and Results

Multi-day Study for Neuropathic Pain Efficacy: A 3-day efficacy study was undertaken wherein the animals (n=3-4/group for shams and 5/group for Chung animals) were administered 10 mg/kg ibudilast or 35% PEG/saline vehicle twice daily and mechanical allodynia was monitored at various time intervals post-dosing. The +1 hr, +2 hr, and +4 hr time points were obtained following the am dose. A pre-dose reading was acquired each day in order to assess durability of efficacy.

Figure 3:
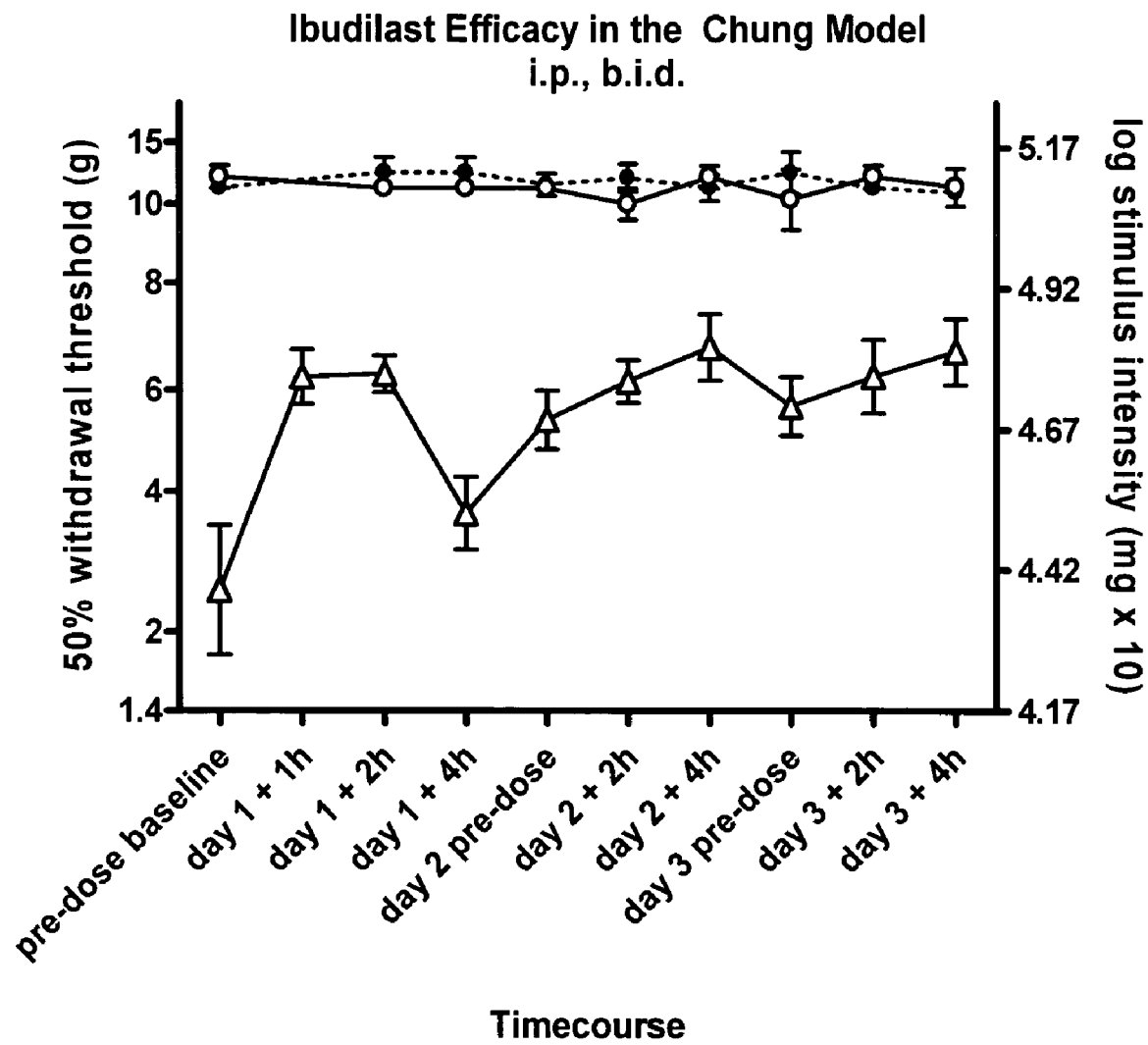
FIG. 3 presents a time course for attenuation of mechanical allodynia following twice daily i.p. administration of ibudilast in the rat Chung model of neuropathic pain, as measured by 50% withdrawal threshold with von Frey fibers. Details of the experiment are provided in Example 2. Data points include error bars representing the mean+/−standard error. Sham 35% PEG/saline (-○-); Sham 10 mg/kg ibudilast (...●...); CCI 10 mg/kg ibudilast (-Δ-). n≧5/group.

As shown in FIG. 3, ibudilast treatment attenuated the magnitude of allodynia in the Chung rats. Notably, sustained attenuation was manifested at +2 hr post-administration starting on the second day of b.i.d. dosing. Moreover, it is clear that within two days of this b.i.d. regimen, the effect was already becoming more sustained such that reversal of neuropathic pain was also evident for as long as 16 hr (pre-dose reading) following ibudilast treatment.

Conclusions

The results of the studies described herein using another classic model of neuropathic pain indicate that systemic administration of ibudilast to Chung rats attenuates mechanical allodynia. Importantly, the somewhat transient nature of the allodynia attenuation observed after a single administration becomes long-lasting by the second day of a bid regimen.

Example 3

Effect of Ibudilast on Mechanical Allodynia in a Rat Model of Taxol-Induced Neuropathic Pain The effect of ibudilast on mechanical allodynia in a rat model of taxol-induced neuropathic pain was assessed as described below.

Methods

Test Agents: Ibudilast was formulated as described above. Ibudilast was administered at 7.5 mg/kg (2.7 ml/kg of 2.8 mg/ml in 35% PEG/saline i.p. each morning (typically 8 am) and pm (typically 3 pm).

Animals: Pathogen-free adult male Sprague-Dawley rats (280-350 g; Harlan Labs) were used in all experiments. Rats were housed in temperature (23+/−3° C.) and light (12:12 light: dark; lights on at 0700 hr) controlled rooms with standard rodent chow and water available ad libitum. Behavioral testing was performed during the light cycle.

Taxol Model: Neuropathic pain was induced by administration of 4 i.p. injections on alternate days (Day 0, 2, 4, and 6) of 1 mg/kg taxol (Paclitaxel®, cumulative dose 4 mg/kg). Neuropathic pain onset was maximal around day 19 post taxol administration (Day 0). Neuropathic pain onset was maximal around day 19 post taxol administration (Day 0). Ibudilast or vehicle control treatment initiated at either day 19 (treatment paradigm) or day 12 (prevention paradigm). Allodynia results were determined prior to the morning administration of vehicle or ibudilast.

Behavioral Measures von Frey Test: The von Frey test was performed within the sciatic or saphenous innervation area of the hindpaws as previously described above for the CCI model. All testing was conducted in the am prior to the morning dose of ibudilast for that day.

Studies and Results

Multi-day Study for Neuropathic Pain Efficacy: 7.5 mg/kg Ibudilast was administered twice daily for 7 days starting day 20 after the first taxol dose (Day 0). Mechanical allodynia was assessed prior to the first dose of ibudilast each day.

Figure 4A:
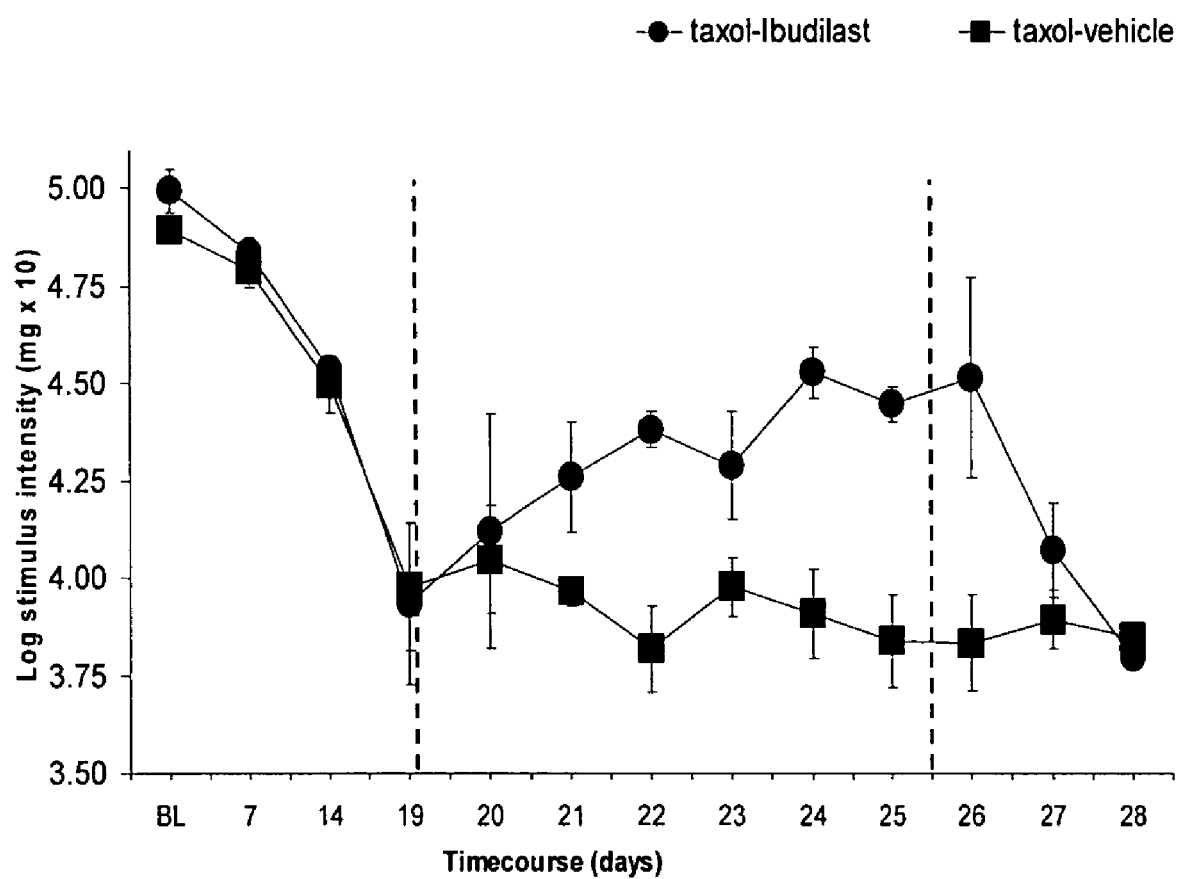
FIGS. 4A and 4B presents a time course of mechanical allodynia in rat models for taxol-induced neuropathic pain, as measured by 50% withdrawal threshold. See Example 3. Ibudilast was administered twice daily with allodynia measurement prior to the morning ibudilast administration.
Figure 4B:
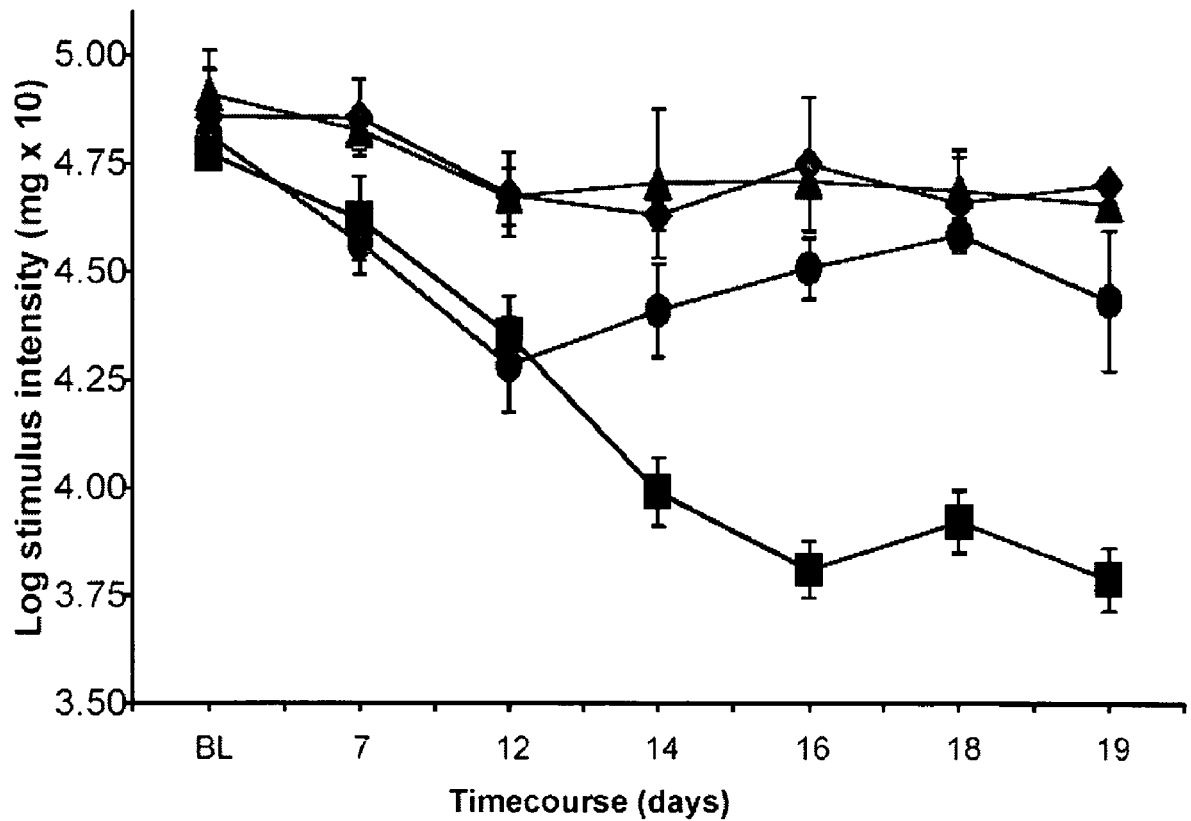

As shown in FIG. 4, administration of ibudilast treatment attenuated the magnitude of allodynia in rats administered taxol. The b.i.d. regimen sustained attenuation of allodynia throughout the dosing period as demonstrated by increased paw withdrawal thresholds prior to daily dosing. Discontinuation of ibudilast administration resulted in return of the rats to an allodynic state within 1 day.

Prevention of Taxol-Induced Neuropathy: A second study was performed identical in nature to the multi-day study described above except that ibudilast or vehicle control administrations were initiated on day 12 just as allodynia was becoming clearly evident. Ibudilast therapy prevented the further neuropathy development and attenuated the low level of allodynia to a level not significantly different from the non-chemotherapy control animals.

Conclusions

The results of the studies described herein using a model of neuropathic pain indicate that systemic administration of ibudilast to rats administered taxol attenuates mechanical allodynia. Attenuation of allodynia is sustained (i.e. apparent overnight to the morning testing period) during b.i.d. administration with rats returning to an allodynic state upon discontinuation of ibudilast administration. Importantly, it was also shown in FIG. 4B that ibudilast treatment could prevent the development of cancer chemotherapy (taxol)-induced neuropathy (allodynia in this example). Such observations with the taxol model of cancer chemotherapy-induced neuropathic pain is expected to extend to other cancer chemotherapeutics known to result in patient neuropathies.

Mechanical allodynia is a common and devastating complication of neuropathic pain in animal models and in humans with chronic neuropathic pain. Hence, the results described herein represent the first known disclosure of the therapeutic use of ibudilast for the treatment of various types of chronic neuropathic pain syndromes in mammals, particularly those syndromes in which mechanical allodynia is a common symptom.

Example 4

Rat Ibudilast Plasma PK and Tissue Distribution

Ibudilast pharmacokinetics and distribution into plasma, muscle, brain, and spinal cord was assessed as follows.

Methods

Test Agents: Ibudilast was prepared in 15% ethanol/saline. Drug stability and concentration were validated by HPLC/MS/MS.

Animals: Pathogen-free adult male Sprague-Dawley rats (280-350 g; Harlan Labs) were used in all experiments. Rats were housed in temperature (23+/−3° C.) and light (12:12 light: dark; lights on at 0700 hr) controlled rooms with standard rodent chow and water available ad libitum. Behavioral testing was performed during the light cycle.

PK Analysis: Rats (n=3/group) were administered 5 mg/kg ibudilast, i.p. and plasma, muscle, brain, and spinal cord were harvested at 5, 15, 60, 180, and 420 min post administration.

Tissue Concentration Analysis: A solution of ibudilast (Haorui) at 0.5 mg/ml in DMSO was used as the working stock. A solution of ibudilast at 0.5 mg/ml in DMSO was prepared using the powdered ibudilast provided with the study samples and used as the working stock. Calibration standards in plasma were prepared by diluting each 0.5 mg/ml stock 1 in 100 into rat plasma to 5000 ng/ml (5 µl+495 µl), then diluting further, to 2.29 ng/ml, by 3-fold serial dilution with plasma. Standards 3, 5 and 7 were used as low, mid and high QC samples, respectively.

Figure 5A:
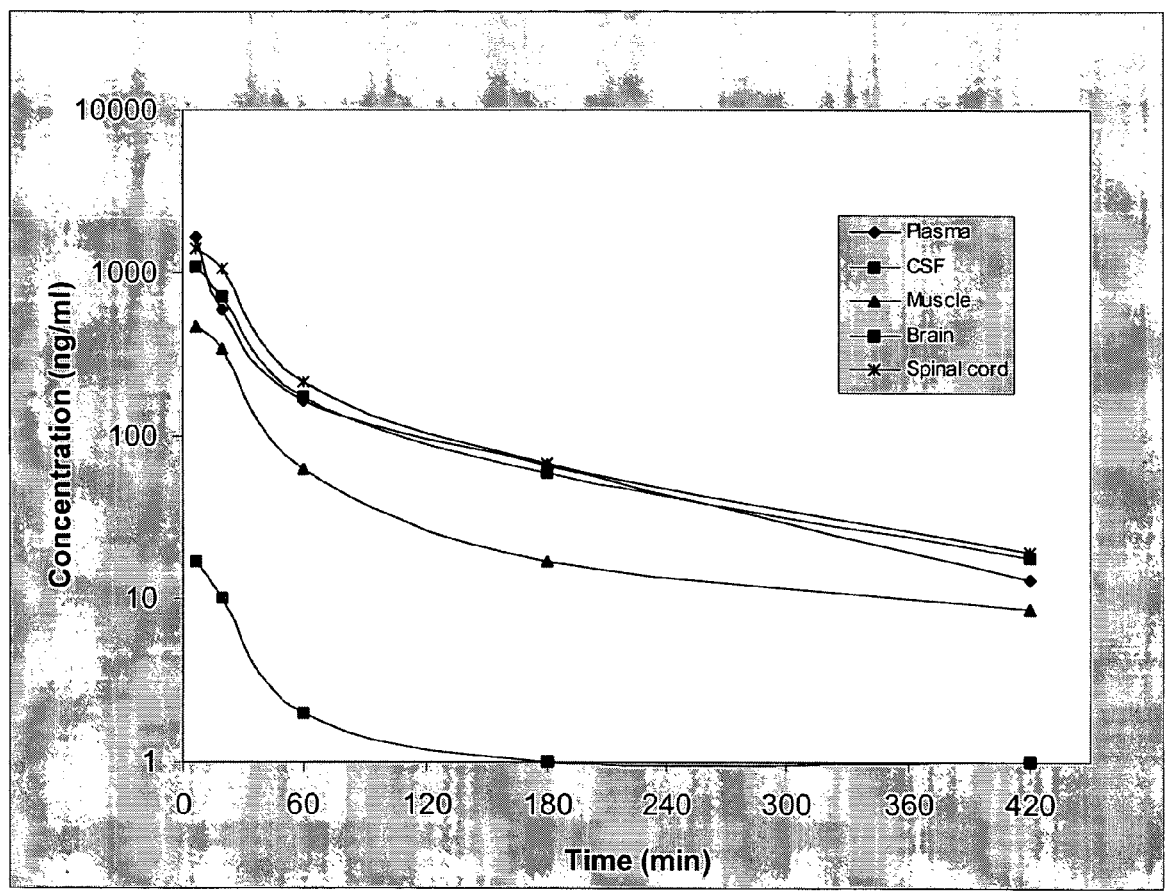
FIGS. 5A and 5B presents ibudilast plasma pharmacokinetics and tissue distribution (5A) in the rat after intraperitoneal administration (5A) or after oral gavage (5B) from two separate studies as described in Example 4. Data points represent mean concentrations of ibudilast for each timepoint in each representative tissue. Plasma and tissues as indicated in inset figure legend. N=3 rats/time point. PK parameters per WinNonlin analysis as described.

Calibration standards, QC and plasma study samples were prepared for HPLC injection by precipitating 25 µl of plasma with 3× volumes (75 µl) of ice cold acetonitrile containing 50 ng/ml diphenhydramine and 100 ng/ml dextromethorphan as the internal standards. Tissue study samples were prepared for HPLC injection by adding 1 µl of water per mg of tissue plus 3× volumes (relative to water) of ice cold acetonitrile containing 50 ng/ml diphenhydramine and 100 ng/ml dextromethorphan as the internal standards, then homogenized with an electric homogenizer. Following centrifugation at 6100 g for 30 minutes, 40 µl of each supernatant was diluted with 200 µl of 0.2% formic acid in water and analyzed by the following LC/MS/MS conditions:

HPLC: Shimadzu VP System
Mobile Phase: 0.2% formic acid in water (A) and in methanol (B)
Column: 2×10 mm Peeke Scientific DuraGel G $C_{18}$ guard cartridge
Injection Volume: 100 µl
Gradient: 5-95% B in 2 minutes after a 0.75 minute wash
Flow Rate: 400 µl/min
Mass Spectrometer: Applied Biosystems/MDS SCIEX API 3000
Interface: TurboIonSpray (ESI) at 400° C.
Ionization Mode: Positive Ion
Q1/Q3 Ions: 231.2/161.2 for ibudilast Studies and Results Intraperitoneal administration of ibudilast yields good plasma concentrations which decline from the Cmax in a biphasic manner. Ibudilast is well distributed to peripheral (e.g. muscle) and central (e.g. brain and spinal cord) tissues. (FIG. 5A). The maximal concentration (Cmax) in plasma and CNS tissues was ~1 µg/mL following i.p. administration of ~5 mg/kg ibudilast formulated as described. The elimination half-life ranged 100-139 min in all tissue compartments.

Conclusions

Figure 5B:
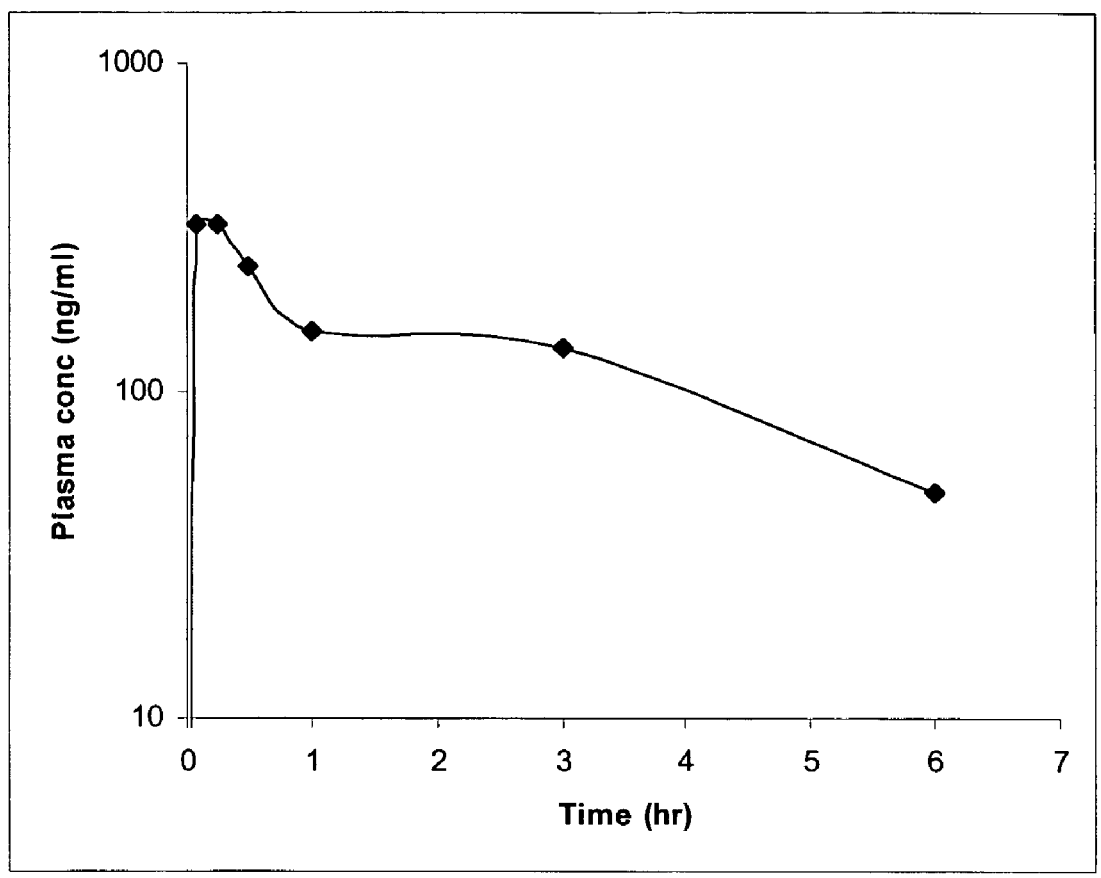

Based on the above, it can be seen that ibudilast is well-distributed peripherally and centrally with tissue kinetics following a single administration similar to that of the plasma compartment. A PK study of ibudilast formulated in 35% PEG400/saline and administered at 21 mg/kg orally to rats is depicted in FIG. 5B. The formulation, dose and route were selected based on our previous results demonstrating attenuation of allodynia in CCI rats under such conditions. The pharmacokinetic parameters derived from the plasma concentration vs time profile are indicated in the table below the figure. Such parameters therefore represent pharmacokinetic correlates with neuropathic pain efficacy.

Example 5

A Prospective, Double-Blind, Randomized, Placebo-Controlled Human Trial of Ibudilast in the Treatment of Neuropathic Pain The purpose of the study is to compare the end of treatment Visual Analog Scale of Pain Index (VASPI) scores with baseline and compare the VASPI score changes among the treatment groups. Safety, tolerability and pharmacokinetics are also assessed.

Method.

This is a double-blind study. The first 7 days of the study consist of a single-blind placebo run-in period. On Study Day 2, subjects are sequentially assigned to receive a single dose of either 10 mg, 20 mg, 30 mg or 40 mg of ibudilast. Pharmacokinetic samples are obtained on Study Day 2. VASPI scores are collected daily. On Study Day 8, subjects who have a favorable response during the run-in period as defined as a 30% change from baseline in VASPI scores, are assigned placebo therapy for the next 14 days. Subjects who did not respond during the run-in period are randomized to receive either BID or TID therapy with ibudilast. Three dose cohorts using 20 mg, 30 mg and 40 mg are used with 20 subjects enrolled in each cohort. Cohorts are filled in a sequential order with the first group of subjects assigned to 20 mg BID or TID, $2^{nd}$ cohort assigned to 30 mg BID or TID and the 3 rd cohort of subjects assigned to 40 mg BID or TID. Dose escalation to higher cohorts is contingent on acceptable safety and tolerability observed in the lower dose cohorts. Adverse events, clinical laboratory results and assessments using the NIH (or EU equivalent) Toxicity Grading Scale are reported. To maintain the blinding of the study medication, all subjects receive TID dosing starting on Day 8 through Day 21.

Subjects are in-house on days that pharmacokinetic parameters are obtained (Days 1, 2, 8, 9, 21 and 22).

Study population: Male or female subjects with diabetic neuropathy or complex regional pain syndrome. Inclusion criteria include: subjects who provide written informed consent, male or female subjects aged 18 to 70 years, diagnosis of diabetic neuropathy or complex regional pain syndrome of at least 6 months duration, VASPI score of 4 or higher for at least 2 weeks prior to the study. Female subjects of child-bearing potential have to be either surgically sterile or using an effective method of contraception. Female subjects of child-bearing potential must have a negative pregnancy test on Study Day 1. Exclusion criteria include subjects with a known hypersensitivity to ibudilast or its components, subjects with any history of a condition which might affect drug absorption, metabolism or excretion, subjects with a history of mental illness, drug addiction, drug abuse or alcoholism, subjects who donated blood in the past 90 days, or have experienced difficulty in donating blood, subjects who have a positive hepatitis B, HIV or drug screen test, female subjects who are pregnant or nursing mothers, and subjects who have received an investigational drug in the past 90 days.

Evaluations include safety, e.g., adverse events, clinical laboratory evaluations, vital signs and 12-lead ECGs, and pharmacokinetics.

Blood samples (1.5 mL) for the assay of ibudilast are collected for the evaluation of plasma levels. Samples are frozen at approximately (−20 or −70° C.) prior to analysis.

TABLE

Schedule of Subject Dosing and Evaluation

| | Screen (Day 0) | Single Dosing | | Days | Multiple Dosing | | | |
|---|---|---|---|---|---|---|---|---|
| | | Day 1 | Day 2 | 3–7 | Day 8 | Day 9 | Day 21 | Day 22 |
| Informed Consent | X | | | | | | | |
| Medical History | X | | | | | | | |
| VASPI | X | X | X | X | | | X | X |
| Neuropathic Pain Scale | X | X | X | X | | | X | X |
| Physical Exam | X | | | | | | | X |
| Clinical Labs (CBC, Chemistry, Urinalysis) | X | | | | | | | X |
| Pregnancy Test | | | X | | | | X | |
| Hepatitis B, HIV &drug screen | X | | | | | | | |
| LFTs only | | | | | | X | | |
| ECG | X | | | | X | | | X |
| Vital Signs (blood pressure and heart rate) | X | X | X | X | | | X | X |
| Dosing* | | | X | X | X | X | X | X |
| PK sample Times | | | | | | | | |
| Pre-dose-Time 0 (e.g. 8:00) | | X | X | | X | X | X | |
| 30 minute (e.g. 8:30) | | | X | | | | X | |
| 1 hour (e.g. 9:00) | | X | X | | X | | X | |
| 2 hours (e.g. 10:00) | | X | X | | X | | X | |
| 4 hours (e.g. 12:00) | | X | X | | X | | X | |

TABLE-continued

Schedule of Subject Dosing and Evaluation

| | Screen | Single Dosing | | Days | Multiple Dosing | | |
|---|---|---|---|---|---|---|---|
| | (Day 0) | Day 1 | Day 2 | 3–7 | Day 8 | Day 9 | Day 21 | Day 22 |
| 6 hours (e.g. 14:00) | | X | | | | | X | |
| 8 hours (e.g. 16:00) | | X | X | | X | | X | |
| 12 hours (e.g. 20:00) | | X | | | | | X | |
| 16 hours (e.g. 24:00) | | | | | | | | |
| 24 hours (e.g. 8:00 D7) | | | | | | | | X |
| 28 hours (e.g. 12:00 D7) | | | | | | | | X |
| 32 hours (e.g. 16:00 D7) | | | | | | | | X |
| Adverse Events | | X | X | X | X | | X | X |
| Concomitant Medications | | X | X | X | X | | X | X |

*Days 1-7 single doses @ 8:00 Days 8-20 BID dosing @ 8:00 and 20:00, TID dosing @ 8:00, 14:00 and 20:00)
Blood draws occur prior to dosing. Meals are given @ 9:00, 13:00, and 18:00)

It is claimed:

1. A method of treating a mammalian subject suffering from existing neuropathic pain, said method comprising:
    selecting a mammalian subject experiencing existing neuropathic pain, wherein said subject does not have multiple sclerosis; and
    administering to said subject an initial therapeutic dosage of 60-100 mg/day of ibudilast, whereby as a result of said administering, the subject experiences relief of said neuropathic pain, wherein no ibudilast is administered prior to the onset of neuropathic pain symptoms.

2. The method of claim 1, wherein said selecting step comprises selecting a mammalian subject suffering from postherpatic neuralgia, trigeminal neuralgia, and neuropathic pain associated with a condition selected from the group consisting of herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, and cancer chemotherapeutic-induced neuropathic pain.

3. The method of claim 1, wherein said administering step comprises systemically administering ibudilast.

4. The method of claim 3, wherein said ibudilast is administered by a route selected from oral, intravenous, subcutaneous, intramuscular, intraperitoneal, intranasal, and sublingual.

5. The method of claim 1, wherein said administering step comprises centrally administering ibudilast by a route selected from intrathecal, intraspinal and intranasal.

6. The method of claim 1, wherein said administering comprises once daily dosing.

7. The method of claim 1, wherein said administering comprises twice or thrice daily dosing.

8. The method of claim 1, wherein said administering is over a time course of at least about a week.

9. The method of claim 1, wherein said administering is over a time course ranging from about one week to 50 weeks.

10. The method of claim 1, wherein said administering step is not accompanied by administration of an anti-emetic.

11. The method of claim 1, whereby said subject is experiencing allodynia, and said administering is effective to relieve allodynia experienced by said subject.

12. The method of claim 1, wherein said administering is effective to attenuate neuropathic pain experienced by said subject for up to at least 16 hours post ibudilast administration.

13. The method of claim 1, wherein said administering step comprises administering ibudilast in combination with an additional agent effective for treating neuropathic pain.

14. The method of claim 13, wherein said additional agent possesses a mechanism of action different from ibudilast.

15. The method of claim 14, wherein said additional agent is selected from the group consisting of gabapentin, memantine, pregabalin, morphine and related opiates, cannabinoids, tramadol, lamotrigine, lidocaine, carbamazepine, duloxetine, milnacipran, and tricyclic antidepressants.

\* \* \* \* \*